US009017694B2

(12) United States Patent
Jin et al.

(10) Patent No.: US 9,017,694 B2
(45) Date of Patent: Apr. 28, 2015

(54) SWINE INFLUENZA HEMAGGLUTININ VARIANTS

(71) Applicant: Medimmune, LLC, Gaithersburg, MD (US)

(72) Inventors: Hong Jin, Cupertino, CA (US); Zhongying Chen, Cupertino, CA (US)

(73) Assignee: MedImmune, LLC, Gaithersburg, MD (US)

( * ) Notice: Subject to any disclaimer, the term of this patent is extended or adjusted under 35 U.S.C. 154(b) by 184 days.

(21) Appl. No.: 13/645,375

(22) Filed: Oct. 4, 2012

(65) Prior Publication Data

US 2013/0115235 A1 May 9, 2013

Related U.S. Application Data

(60) Provisional application No. 61/545,055, filed on Oct. 7, 2011.

(51) Int. Cl.
| | |
|---|---|
| *C07H 21/00* | (2006.01) |
| *C07K 14/11* | (2006.01) |
| *C12N 7/00* | (2006.01) |
| *A61K 39/145* | (2006.01) |
| *C07K 14/005* | (2006.01) |

(52) U.S. Cl.
CPC ............... *C12N 7/00* (2013.01); *A61K 39/145* (2013.01); *C07K 14/11* (2013.01); *C07K 14/005* (2013.01); *C12N 2760/16121* (2013.01); *C12N 2760/16151* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 5,166,057 | A | 11/1992 | Palese et al. |
| 5,482,856 | A | 1/1996 | Fell, Jr. et al. |
| 5,922,326 | A | 7/1999 | Murphy et al. |
| 6,544,785 | B1 | 4/2003 | Palese et al. |
| 8,012,736 | B2 | 9/2011 | Hoffman et al. |
| 8,088,393 | B2 * | 1/2012 | Jin .............................. 424/206.1 |
| 8,114,415 | B2 | 2/2012 | Hoffmann et al. |
| 2002/0164770 | A1 | 11/2002 | Hoffmann |
| 2009/0175907 | A1 | 7/2009 | Hoffman et al. |

OTHER PUBLICATIONS

Lu et al., "Single amino acid substitutions in the hemagglutinin of influenza A/Singapore/21/04 (H3N2) increase virus growth in embryonated chicken eggs" Vaccine (2006) 24:6691-6693.
Abelin et al., (2010). Lessons from pandemic influenza A (H1N1): the research-based vaccine industry's perspective. *Vaccine* 29(6), 1135-8.
Altschul et al., J Mol Biol 215:403-410 (1990).
Baron & Barrett (1997) J. Virol. 71: 1265-1271.
Barr et al., "A new pandemic influenza A(H1N1) genetic variant predominated in the winter 2010 influenza season in Australia. New Zealand and Singapore," Euro Surveillance. vol. 15, No. 42. Jan. 1, 2010.
Beaucage and Caruthers, Tetrahedron Letts 22(20):1859 1862, (1981).
Belshe et al. (1998) The efficacy of live attenuated, cold-adapted, trivalent, intranasal influenza virus vaccine in children N Engl J Med 338:1405-12.
Bitter et al., "Expression and secretion vectors for yeast," (1987); Methods in Enzymology 153:516-544.
Chen et al. (2010). Generation of live attenuated novel influenza virus A/California/7/09 (H1N1) vaccines with high yield in embryonated chicken eggs. *J Virol* 84(1), 44-51.
Collins et al. "Production of infectious human respiratory syncytial virus from cloned cDNA confirms an essential role for the transcription elongation factor from the 5' proximal open reading frame of the M2 mRNA in gene expression and provides a capability for vaccine development," (1995) Proc. Natl. Acad. Sci. USA 92(25):11563-11567.
Database UniProt [Online] May 3, 2011, IISubName: Full=Hemagglutinin; Flags: Precursor; Fragment; . XP002692410. retrieved from EBI accession No. UniProt:F0TUB8 Database accession No. F0TUB8.
Database UniProt [Online] Sep. 21, 2011. IISubName: Full=Hemagglutinin; Flags:Precursor; , XP002692409. retrieved from EBI accession No. UniProt:F8IWU0 Database accession No. F8IWU0.
Durbin et al. "Recovery of Infectious Human Parainfluenza Virus Type 3 from cDNA" (1997) Virology 235:323-332.
Enami et al., "Introduction of site-specific mutations into the genome of influenza virus," Proc Natl Acad Sci U S A. May 1990; 87(10): 3802-3805.
Feng & Doolittle "Progressive sequence alignment as a prerequisite to correct phylogenetic trees," (1987) J. Mol. Evol. 35:351-360.
Fromm et al., "Expression of genes transferred into monocot and dicot plant cells by electroporation.," Proc Natl Acad Sci USA 82, 5824-5828 (1985).
Gassen et al. (2000) J. Virol. 74:10737-44.
GeneBank Accession No. AEH59413.1 hemagglutinin [Influenza A virus (A/Singapore/TT67/2011(H1N1))] Jun. 10, 2011.
Gherna "The ATCC Catalogue of Bacteria and Bacteriophage" (1992) Gherna et al. (eds.) published by the ATCC.
Gillam & Smith, "Site-specific mutagenesis using synthetic oligodeoxyribonucleotide primers: I. Optimum conditions and minimum oligodeoxyribonucleotide length," Gene 8:81-97 (1979).
He et al. (1997) Virology 237:249-260.
Henikoff and Henikoff (1992) Proc. Natl. Acad. Sci. USA 89: 10915-10919.
Higgins & Sharp "Fast and sensitive multiple sequence alignments on a microcomputer," (1989) CABIOS5:151-153.

(Continued)

Primary Examiner — Mary E Mosher
Assistant Examiner — Myron Hill
(74) Attorney, Agent, or Firm — Grant IP, Inc.

(57) ABSTRACT

The technology relates in part to modified influenza viruses useful for vaccine development. Polypeptides, polynucleotides, methods, compositions, and vaccines comprising influenza hemagglutinin and neuraminidase variants are provided.

19 Claims, 14 Drawing Sheets

(56) References Cited

OTHER PUBLICATIONS

Hoffman & Banerjee (1997) J. Virol. 71: 4272-4277.
Hoffmann, E., 2000, PNAS, 97(11):6108-6113.
Jin, et al., (2003). Multiple amino acid residues confer temperature sensitivity to human influenza virus vaccine strains (FluMist) derived from cold-adapted A/Ann Arbor/6/60. Virology 306(1), 18-24.
Karlin & Altschul, "Applications and statistics for multiple high-scoring segments in molecular sequences," Proc Natl Acad Sci USA 90:5873-5787 (1993).
Kato et al. (1996) Genes to Cells 1:569-579.
Kim et al., "Safety and antigenicity of temperature sensitive (TS) mutant respiratory syncytial virus (RSV) in infants and children," Pediatrics 52:56-63 (1973).
Klein et al., "High-velocity microprojectiles for delivering nucleic acids into living cells." Nature 327, 70-73 (1987).
Lamb et al., (2001). Orthomyxoviridae: The viruses and their replication. In "Fields Virology" (D. M. Knipe, and P. M. Howley, Eds.), vol. 1, pp. 1487-1531. 2 vols. Lippincott Williams & Wilkins, Philadelphia, PA.
Lawson et al. (1995) Proc. Natl. Acad. Sci. USA 92: 4477-4481.
Logan and Shenk "Adenovirus tripartite leader sequence enhances translation of mRNAs late after infection," (1984) Proc Natl Acad Sci 81:3655-3659.
Lu et al., (2005). Improvement of influenza A/Fujian/411/02 (H3N2) virus growth in embryonated chicken eggs by balancing the hemagglutinin and neuraminidase activities, using reverse genetics. *J Virol* 79(11), 6763-71.
Luytjes et al. (1989) Cell 59:1107-1113.
Maassab (1967) Adaptation and growth characteristics of influenza virus at 25 degrees C Nature 213:612-4.
Murphy & Coelingh (2002) Principles underlying the development and use of live attenuated cold-adapted influenza A and B virus vaccines Viral Immunol 15:295-323.
Needham VanDevanter et al., Nucleic Acids Res, 12:6159-6168 (1984).
Needleman & Wunsch, J Mol Biol 48:443 (1970).
Nichol et al. (1999) Effectiveness of live, attenuated intranasal influenza virus vaccine in healthy, working adults: a randomized controlled trial JAMA 282:137-44.
Park et al. (1991) Proc. Natl. Acad. Sci. USA 88: 5537-5541.
Paul "Fundamental Immunology", W. E. Paul, ed., Raven Press, N.Y. (1999).
Pearson & Lipman, "Improved tools for biological sequence comparison," Proc Natl Acad Sci USA 85:2444 (1988).
Radecke et al.(1995) EMBO J. 14:5773-5784.
Roberts, et al., Nature, 328:731 (1987).
Robertson et al., "The development of vaccine viruses against pandemic A(H1N1) Influenza," Vaccine, Elsevier Ltd, GB, vol. 29, No. 9, Dec. 14, 2010, pp. 1836-1843.
Schild, et al., "Antigenic variation in current human type A influenzaviruses: Antigenic characteristics of the variants and their geographic distribution," Bull. Wld. Hlth. Org. (1973) 48:269-278.
Schneider, B., et al., "Functional Purification of a Bacterial ATP-Binding Cassette Transporter Protein (MalK) from the Cytoplasmic Fraction of an Overproducing Strain," Protein Expr Purif 6(1):10-14 (1995).
Schnell et al. (1994) EMBO J. 13: 4195-4203.
Smith & Waterman, "Comparison of biosequences," Adv Appl Math 2:482-489 (1981).
Smith et al. (2009). Origins and evolutionary genomics of the 2009 swine-origin H1N1 influenza A epidemic. *Nature* 459(7250), 1122-5.
Thompson, et al. (2003). Mortality associated with influenza and respiratory syncytial virus in the United States. *JAMA* 289(2), 179-86.
Thompson, J. D. et al. "Clustal W: improving the sensitivity of progressive multiple sequence alignment through sequence weighting, position-specific gap penalties and weigh matrix choice," (1994) Nucl. Acids. Res. 22: 4673-4680.
Van Heeke & Schuster "Expression of human asparagine synthetase in *Escherichia coli*" (1989) J Biol Chem 264:5503-5509.
Wright et al., "Administration of a highly attenuated, live respiratory syncytial virus vaccine to adults and children," Infect. Immun. 37:397-400 (1982).
International Search Report and Written Opinion dated: Jun. 20, 2013 in International Application No. PCT/US2012/058807 filed: Oct. 4, 2012.
Invitation to Pay Additional Fees and Partial Search Report dated: March 5, 2013 in International Application No. PCT/US2012/058807 filed: Oct. 4, 2012.
International Preliminary Report on Patentability mailed on Apr. 17, 2014 in International Application No. PCT/US2012/058807, filed Oct. 4, 2012 and published as WO 2013/130132 on Sep. 6, 2013.

\* cited by examiner

Figure 1A
Figure 1B
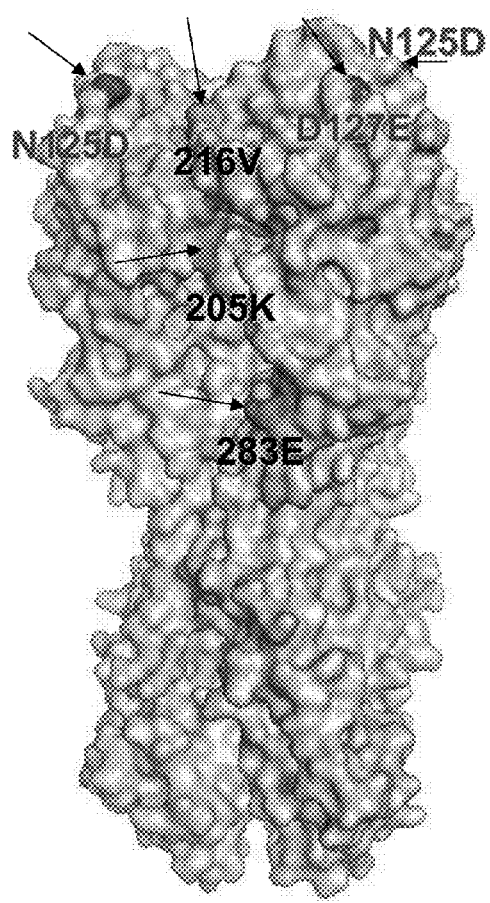
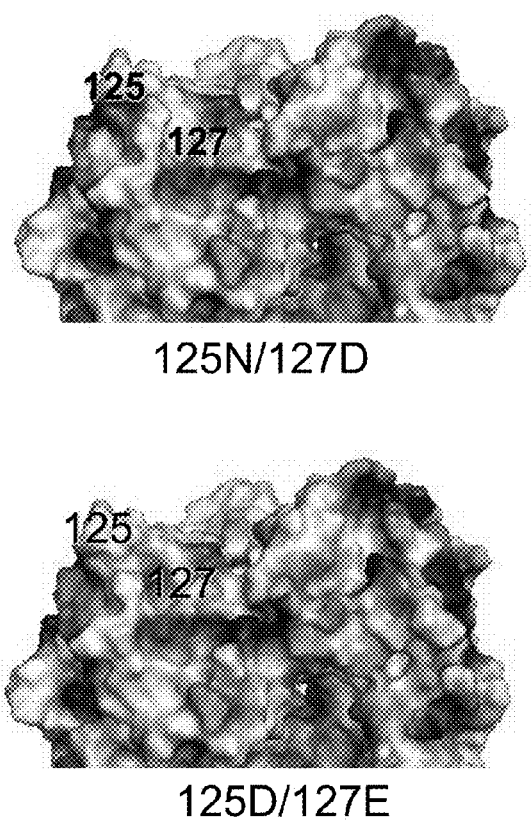
125N/127D
125D/127E

Figure 4

A/Gilroy/231/2011 HA amino acid sequence (SEQ ID NO:28)

```
mkailvvllytfaianadtlcigyhannstdtvdtvleknvtvthsvnlledkhngklcklr
gvaplhlgkcniagwilgnpeceslstasswsyivetsssdngtcypgdfinyeelreqlss
vssferfeifpktsswpnhdsnkgvtaacphagaksfyknliwlvkkgnsypklsksyindk
gkevlvlwgihhpstsadqqslyqnadayvfvgtskyskkfkpeiavrpkvrdqegrmnyyw
tlvepgdkitfeatgnllvpryafamernagsgiiisdtpvhdcnttcqtpegaintslpfq
nihpitlgkcpkyvkstklrlatglrnvpsiqsrglfgaiagfieggwtgmvdgwygyhhqn
eqgsgyaadlkstqnaidkitnkvnsviekmntqftavgkefnhlekrienlnkkvddgfld
iwtynaellvllenertldyhdsnvknlyekvrsqlknnakeigngcfefyhkcdntcmesv
kngtydypkyseeaklnreeidgvklestriyqilaiystvasslvlvvslgaisfwmcsng
slqcrici
```

Figure 5

A/Gilroy/231/2011 HA nucleotide sequence (SEQ ID NO:2)

```
gtgaaggcaatactagtagttctgctatatacatttgcaaccgcaaatgcagacacattatg
tataggttatcatgcgaacaattcaacagacactgtagacacagtactagaaaagaatgtaa
cagtaacacactctgttaaccttctagaagacaagcataacgggaaattatgcaaactaaga
ggggtagccccattgcatttgggtaaatgtaacattgctggctggatcctgggaaatccaga
gtgtgaatcactctccacagcaagctcatggtcctacattgtggaaacatctagttcagaca
atggaacgtgttacccaggagatttcatcgattatgaggagctaagagaacaattgagctca
gtgtcatcatttgaaaggtttgagatattccccaagacaagttcatggcccgatcatgamtc
gaacaaaggtgtaacggcagcatgtcctcatgctggagcaaaaagcttctacaaaaatttaa
tatggctagttaaaaaaggaaattcatacccaaagctcagcaaatcctacattaatgataaa
gggaaagaagtcctcgtgctatggggcattcaccatccatctactagtgctgaccaacaaag
tctctatcagaatgcagatgcatatgtttttgtggggacatcaagatacagcaagaagttca
agccggaaatagcaataagacccaaagtgagggatcaagaagggagaatgaactattactgg
acactagtagagccgggagacaaaataacattcgaagcaactggaaatctagtggtaccgag
atatgcattcgcaatggaagaaatgctggatctggtattatcatttcagatacaccagtcc
acgattgcaatacaacttgtcagacacccaagggtgctataaacaccagcctcccatttcag
aatatacatccgatcacaattggaaaatgtccaaatatgtaaaagcacaaaattgagact
ggccacaggattgaggaatgtcccgtctattcaatctagaggcctatttggggccattgcg
gtttcattgaaggggggtggacagggatggtagatggatggtacggttatcaccatcaaaat
gagcagggtcaggatatgcagccgacctgaagagcacacagaatgccattgacaagattac
taacaaagtaaattctgttattgaaaagatgaatacacagttcacagcagtaggtaaagagt
tcaaccacctggaaaaaagaatagagaatttaaataaaaagttgatgatggtttcctggac
atttggacttacaatgccgaactgttggttctattggaaaatgaaagaactttggactacca
cgattcaaatgtgaagaacttatatgaaaaggtaagaagccagttaaaaaacaatgccaagg
aaattggaaacggctgctttgaattttaccacaaatgcgataacacgtgcatggaaagtgtc
aaaaatgggacttatgactacccaaaatactcagaggaagcaaaattaaacagagaagaaat
agatggggtaaagctggaatcaacaaggatttaccagattttggcgatctattcaactgtcg
ccagttcattggtactggtagtctccctgggggcaatcagtttctggatgtgctctaatggg
tctctacagtgtagaatatgtatttaa
```

Figure 6

A/Gilroy/231/2011 NA Amino Acid Sequence (SEQ ID NO:3)

mnpnqkiitigsvcmtigmanlilqigniisiwishsiqlgnqsqietcnqsvityenntwvnq
tyvnisntnfaagqsvvsvklagnsslcpvsgwaiyskdnsirigskgdvfvirepfiscsple
crtffltqgallndkhsngtikdrspyrtlmscpigevpspynsrfesvawsasachdginwlt
igisgpdngavavlkyngiitdtikswrnsilrtqesecacvngscftimtdgpsdgqasykif
riekgkivksvemnapnyhyeecscypdsseitcvcrdnwhgsnrpwvsfnqnleyqigyicsg
ifgdnprpndktgscgpvssngangvkgfsfkygngvwigrtksissrkgfemiwdpngwtgtd
nnfsikqdivginewsgysgsfvqhpeltgldcirpcfwvelirgrpkentiwtsgssmsfcgv
nsdtvgwswpdgaelpftidk

Figure 7

A/Gilroy/231/2011 NA nucleotide sequence (SEQ ID NO:4)

atgaatccaaaccaaaagataataaccattggttcggtctgtataacaattggaatggctaact
taatattacaaattggaaacataatctcaatatggattagccactcaattcaacttgggaatca
aatcagattgaaacatgcaatcaaagcgtcattacttatgaaaacaacacttgggtaaatcag
acatatgttaacatcagcaacaccaactttgctgctggacagtcagtggtttccgtgaaattag
cgggcaattcctctctctgccctgttagtggatgggctatatacagtaaagacaacagtataag
aatcggttccaaggggggatgtgtttgtcataagggaaccattcatatcatgctccccttggaa
tgcagaaccttcttcttgactcaaggggccttgctaaatgacaaacattccaatggaaccatta
aagacaggagcccatatcgaaccctaatgagctgtcctattggtgaagttccctctccatacaa
ctcaagatttgagtcagtcgcttggtcagcaagtgcttgtcatgatggcatcagttggctaaca
attggaatttctggcccagacaatggggcagtggctgtgttaaagtacaacggcataataacag
acactatcaagagttggagaaacaatatattgagaacacaagagtctgaatgtgcatgtgtaaa
tggttcttgttttactgtaatgaccgatggaccaagtgatggacaggcctcatacaagatcttc
agaatagaaagggaaagatagtcaaatcagtcgaaatgaatgcccctaattatcactatgagg
aatgctcctgttatcctgattctagtgaaatcacatgtgtgtgcagggataactggcatggctc
gaatcgaccgtgggtgtctttcaaccagaatctggaatatcagataggatacatatgcagtggg
attttcggagacaatccacgccctaatgataagacaggcagttgtggtccagtatcgtctaatg
gagcaaatggagtaaaaggattttcattcaaatacggcaatggtgtttggatagggagaactaa
aagcattagttcaagaaacggttttgagatgatttgggatccgaacggatggactgggacagac
aataacttctcaataaagcaagatatcgtaggaataaatgagtggtcaggatatagcgggagtt
ttgttcagcatccagaactaacagggctggattgtataaaaaccttgcttctgggttgaactaat
cagagggcgacccaaagagaacacaatctggactagcgggagcagcatatcctttttgtggtgta
aacagtgacactgtgggttggtcttggccagacggtgctgagttgccatttaccattgacaagt
aa

Figure 8

```
                          1                                                    50
    A/Brisbane/10/10_HA   MKAILVVLLY TFATANADTL CIGYHANNST DTVDTVLEKN VTVTHSVNLL
    A/California/04/09_HA MKAILVVLLY TFATANADTL CIGYHANNST DTVDTVLEKN VTVTHSVNLL
     A/Gilroy/231/11_HA   MKAILVVLLY TFAIANADTL CIGYHANNST DTVDTVLEKN VTVTHSVNLL
                          51                                                  100
    A/Brisbane/10/10_HA   EDKHNGKLCK LRGVAPLHLG KCNIAGWILG NPECESLSTA SSWSYIVETS
    A/California/04/09_HA EDKHNGKLCK LRGVAPLHLG KCNIAGWILG NPECESLSTA SSWSYIVETP
     A/Gilroy/231/11_HA   EDKHNGKLCK LRGVAPLHLG KCNIAGWILG NPECESLSTA SSWSYIVETS
                          101                       H1 mature protein # 125 127  150
    A/Brisbane/10/10_HA   SSDNGTCYPG DFIDYEELRE QLSSVSSFER FEIFPKTSSW PDHESNKGVT
    A/California/04/09_HA SSDNGTCYPG DFIDYEELRE QLSSVSSFER FEIFPKTSSW PNHDSNKGVT
     A/Gilroy/231/11_HA   SSDNGTCYPG DFINYEELRE QLSSVSSFER FEIFPKTSSW PNHDSNKGVT
                          151                                                 200
    A/Brisbane/10/10_HA   AACPHAGAKS FYKNLIWLVK KGNSYPKLSK SYINDKGKEV LVLWGIHHPS
    A/California/04/09_HA AACPHAGAKS FYKNLIWLVK KGNSYPKLSK SYINDKGKEV LVLWGIHHPS
     A/Gilroy/231/11_HA   AACPHAGAKS FYKNLIWLVK KGNSYPKLSK SYINDKGKEV LVLWGIHHPS
                          201                                                 250
    A/Brisbane/10/10_HA   TSADQQSLYQ NADAYVFVGT SRYSKKFKPE IAIRPKVRDQ EGRMNYYWTL
    A/California/04/09_HA TSADQQSLYQ NADTYVFVGS SRYSKKFKPE IAIRPKVRDQ EGRMNYYWTL
     A/Gilroy/231/11_HA   TSADQQSLYQ NADAYVFVGT SKYSKKFKPE IAVRPKVRDQ EGRMNYYWTL
                          251                                                 300
    A/Brisbane/10/10_HA   VEPGDKITFE ATGNLVVPRY AFAMERNAGS GIIISDTPVH DCNTTCQTPK
    A/California/04/09_HA VEPGDKITFE ATGNLVVPRY AFAMERNAGS GIIISDTPVH DCNTTCQTPK
     A/Gilroy/231/11_HA   VEPGDKITFE ATGNLLVPRY AFAMERNAGS GIIISDTPVH DCNTTCQTPE
                          301                                                 350
    A/Brisbane/10/10_HA   GAINTSLPFQ NIHPITIGKC PKYVKSTKLR LATGLRNVPS IQSRGLFGAI
    A/California/04/09_HA GAINTSLPFQ NIHPITIGKC PKYVKSTKLR LATGLRNIPS IQSRGLFGAI
     A/Gilroy/231/11_HA   GAINTSLPFQ NIHPITLGKC PKYVKSTKLR LATGLRNVPS IQSRGLFGAI
                          351                                                 400
    A/Brisbane/10/10_HA   AGFIEGGWTG MVDGWYGYHH QNEQGSGYAA DLKSTQNAID KITNKVNSVI
    A/California/04/09_HA AGFIEGGWTG MVDGWYGYHH QNEQGSGYAA DLKSTQNAID EITNKVNSVI
     A/Gilroy/231/11_HA   AGFIEGGWTG MVDGWYGYHH QNEQGSGYAA DLKSTQNAID KITNKVNSVI
                          401                                                 450
    A/Brisbane/10/10_HA   EKMNTQFTAV GKEFNHLEKR IENLNKKVDD GFLDIWTYNA ELLVLLENER
    A/California/04/09_HA EKMNTQFTAV GKEFNHLEKR IENLNKKVDD GFLDIWTYNA ELLVLLENER
     A/Gilroy/231/11_HA   EKMNTQFTAV GKEFNHLEKR IENLNKKVDD GFLDIWTYNA ELLVLLENER
                          451                                                 500
    A/Brisbane/10/10_HA   TLDYHDSNVK NLYEKVRSQL KNNAKEIGNG CFEFYHKCDN TCMESVKNGT
    A/California/04/09_HA TLDYHDSNVK NLYEKVRSQL KNNAKEIGNG CFEFYHKCDN TCMESVKNGT
     A/Gilroy/231/11_HA   TLDYHDSNVK NLYEKVRSQL KNNAKEIGNG CFEFYHKCDN TCMESVKNGT
                          501                                                 550
    A/Brisbane/10/10_HA   YDYPKYSEEA KLNREEIDGV KLESTRIYQI LAIYSTVASS LVLVVSLGAI
    A/California/04/09_HA YDYPKYSEEA KLNREEIDGV KLESTRIYQI LAIYSTVASS LVLVVSLGAI
     A/Gilroy/231/11_HA   YDYPKYSEEA KLNREEIDGV KLESTRIYQI LAIYSTVASS LVLVVSLGAI
                          551        566
    A/Brisbane/10/10_HA   SFWMCSNGSL QCRICI
    A/California/04/09_HA SFWMCSNGSL QCRICI
     A/Gilroy/231/11_HA   SFWMCSNGSL QCRICI
```

Figure 9

```
                      1                                                    50
A/Brisbane/10/10_NA   MNPNQKIITI GSVCITIGMA NLILQIGNII SIWISHSIQL GNQNQIETCN
A/California/04/09_NA MNPNQKIITI GSVCMTIGMA NLILQIGNII SIWISHSIQL GNQNQIETCN
   A/Gilroy/231/11_NA MNPNQKIITI GSVCMTIGMA NLILQIGNII SIWISHSIQL GNQSQIETCN
                      51                                                   100
A/Brisbane/10/10_NA   QSVITYENNT WVNQTYVNIS NTNFAAGQSV VSVKLAGNSS LCPVSGWAIY
A/California/04/09_NA QSVITYENNT WVNQTYVNIS NTNFAAGQSV VSVKLAGNSS LCPVSGWAIY
   A/Gilroy/231/11_NA QSVITYENNT WVNQTYVNIS NTNFAAGQSV VSVKLAGNSS LCPVSGWAIY
                      101                                                  150
A/Brisbane/10/10_NA   SKDNSIRIGS KGDVFVIREP FISCSPLECR TFFLTQGALL NDKHSNGTIK
A/California/04/09_NA SKDNSVRIGS KGDVFVIREP FISCSPLECR TFFLTQGALL NDKHSNGTIK
   A/Gilroy/231/11_NA SKDNSIRIGS KGDVFVIREP FISCSPLECR TFFLTQGALL NDKHSNGTIK
                      151                                                  200
A/Brisbane/10/10_NA   DRSPYRTLMS CPIGEVPSPY NSRFESVAWS ASACHDGISW LTIGISGPDN
A/California/04/09_NA DRSPYRTLMS CPIGEVPSPY NSRFESVAWS ASACHDGINW LTIGISGPDN
   A/Gilroy/231/11_NA DRSPYRTLMS CPIGEVPSPY NSRFESVAWS ASACHDGINW LTIGISGPDN
                      201                                                  250
A/Brisbane/10/10_NA   GAVAVLKYNG IITDTIKSWR NNILRTQESE CACVNGSCFT VMTDGPSDGQ
A/California/04/09_NA GAVAVLKYNG IITDTIKSWR NNILRTQESE CACVNGSCFT VMTDGPSNGQ
   A/Gilroy/231/11_NA GAVAVLKYNG IITDTIKSWR NSILRTQESE CACVNGSCFT IMTDGPSDGQ
                      251                                                  300
A/Brisbane/10/10_NA   ASYKIFRIEK GKIVKSVEMN APNYHYEECS CYPDSSEITC VCRDNWHGSN
A/California/04/09_NA ASYKIFRIEK GKIVKSVEMN APNYHYEECS CYPDSSEITC VCRDNWHGSN
   A/Gilroy/231/11_NA ASYKIFRIEK GKIVKSVEMN APNYHYEECS CYPDSSEITC VCRDNWHGSN
                      301                                                  350
A/Brisbane/10/10_NA   RPWVSFNQNL EYQIGYICSG IFGDNPRPND KTGSCGPVSS NGANGVKGFS
A/California/04/09_NA RPWVSFNQNL EYQIGYICSG IFGDNPRPND KTGSCGPVSS NGANGVKGFS
   A/Gilroy/231/11_NA RPWVSFNQNL EYQIGYICSG IFGDNPRPND KTGSCGPVSS NGANGVKGFS
                      351                                                  400
A/Brisbane/10/10_NA   FKYGNGVWIG RTKSISSRNG FEMIWDPNGW TGTDNNFSIK QDIVGINEWS
A/California/04/09_NA FKYGNGVWIG RTKSISSRNG FEMIWDPNGW TGTDNNFSIK QDIVGINEWS
   A/Gilroy/231/11_NA FKYGNGVWIG RTKSISSRKG FEMIWDPNGW TGTDNNFSIK QDIVGINEWS
                      401                                                  450
A/Brisbane/10/10_NA   GYSGSFVQHP ELTGLDCIKP CFWVELIRGR PKENTIWTSG SSISFCGVNS
A/California/04/09_NA GYSGSFVQHP ELTGLDCIRP CFWVELIRGR PKENTIWTSG SSISFCGVNS
   A/Gilroy/231/11_NA GYSGSFVQHP ELTGLDCIRP CFWVELIRGR PKENTIWTSG SSMSFCGVNS
                      451            469
A/Brisbane/10/10_NA   DTVGWSWPDG AELPFTIDK
A/California/04/09_NA DTVGWSWPDG AELPFTIDK
   A/Gilroy/231/11_NA DTVGWSWPDG AELPFTIDK
```

```
                                                                              Section 8
               (358)  358         370         380         390         408
A/Brisbane/10/10 HA (358)  WTGMVDGWYGYHHQNEQGSGYAADLKSTQNAIDK TNKVNSVIEKMNTQFT
A/California/04/09 HA (358)  WTGMVDGWYGYHHQNEQGSGYAADLKSTQNAIDK TNKVNSVIEKMNTQFT
A/Gilroy/231/11 HA (358)  WTGMVDGWYGYHHQNEQGSGYAADLKSTQNAIDK TNKVNSVIEKMNTQFT
        Consensus (358)  WTGMVDGWYGYHHQNEQGSGYAADLKSTQNAIDK TNKVNSVIEKMNTQFT
                                                                              Section 9
               (409)  409         420         430         440         459
A/Brisbane/10/10 HA (409)  AVGKEFNHLEKRIENLNKKVDDGFLDIWTYNAELLVLLENERTLDYHDSNV
A/California/04/09 HA (409)  AVGKEFNHLEKRIENLNKKVDDGFLDIWTYNAELLVLLENERTLDYHDSNV
A/Gilroy/231/11 HA (409)  AVGKEFNHLEKRIENLNKKVDDGFLDIWTYNAELLVLLENERTLDYHDSNV
        Consensus (409)  AVGKEFNRLEKRIENLNKKVDDGFLDIWTYNAELLVLLENERTLDYHDSNV
                                                                              Section 10
               (460)  460         470         480         490         500         510
A/Brisbane/10/10 HA (460)  KNLYEKVRSQLKNNAKEIGNGCFEFYHKCDNTCMESVKNGTYDYPKYSEEA
A/California/04/09 HA (460)  KNLYEKVRSQLKNNAKEIGNGCFEFYHKCDNTCMESVKNGTYDYPKYSEEA
A/Gilroy/231/11 HA (460)  KNLYEKVRSQLKNNAKEIGNGCFEFYHKCDNTCMESVKNGTYDYPKYSEEA
        Consensus (460)  KNLYEKVPSQLKNNAKEIGNGCFEFYHKCDNTCMESVKNGTYDYPKYSEEA
                                                                              Section 11
               (511)  511         520         530         540         550         561
A/Brisbane/10/10 HA (511)  KLNREEIDGVKLESTRIYQILAIYSTVASSLVLVVSLGAISFWMCSNGSLQ
A/California/04/09 HA (511)  KLNREEIDGVKLESTRIYQILAIYSTVASSLVLVVSLGAISFWMCSNGSLQ
A/Gilroy/231/11 HA (511)  KLNREEIDGVKLESTRIYQILAIYSTVASSLVLVVSLGAISFWMCSNGSLQ
        Consensus (511)  KLNREEIDGVKLESTRIYQILAIYSTVASSLVLVVSLGAISFWMCSNGSLQ
                                                                              Section 12
               (562)  562 566
A/Brisbane/10/10 HA (562)  CRICI
A/California/04/09 HA (562)  CRICI
A/Gilroy/231/11 HA (562)  CRICI
        Consensus (562)  CRICI
```

Figure 11

| HA | A/Gilroy/231/CA/2011 HA 125D/127E | A/Gilroy/231/CA/2011 HA 125D/127E | A/Brisbane/10/10 | A/CA/09 119E, 186D | A/Gilroy/231/CA/2011 HA 125E/127E | A/Gilroy/231/CA/2011 HA 125E/127E |
|---|---|---|---|---|---|---|
| NA | A/Gilroy/231/CA/2011 | A/Brisbane/10/10 | A/Brisbane/10/10 | A/CA/09 | A/Gilroy/231/CA/2011 | A/Brisbane/10/10 |
| Virus titer ($\log_{10}$PFU/ml) | 7.1 | 7.7 | 8.1 | 8 | 6.7 | 7.2 |
| Plaque Image | | | | | | |

Figure 12

|  | | FFA | TCID50 | PFU |
|---|---|---|---|---|
| FLU 1464 | ca A/New Hampshire/02/10 | 7.4 | 3.4 | not visible |
| FLU 1465 | ca A/South Carolina/02/10-127E | 7.7 | 4.2 | not visible |
| FLU 1467 | ca A/Christchurch/16/10 | 8.4 | 8.4 | 7.8 |
| FLU 1468 | ca A/Hong Kong/2212/10 | 7.8 | 7.7 | 7.2 |
| FLU 1447 | 6:2 A/Gilroy/231/CA/2011-125D/127E | 7.9 | 7.3 | 6.4 |
| FLU 1462 | 6:1:1 A/Gilroy/231/CA/2011-125D/127E/ Bris NA | 8.3 | 8.4 | 7.4 |
| FLU 1334 | ca A/Bris/10/10 (Positive) | 8.5 | 8.9 | 7.8 |

Figure 13

| Virus lot | ca A/Gilroy/231/CA/2011 with changes in HA | Additional site changes in HA | Virus titer (Log$_{10}$PFU/ml) |
|---|---|---|---|
| FLU 1456-13 | 125D +127E | N97D | 1X10$^7$ |
| FLU 1457-16 | 125D +127E | K205R | 5X10$^6$ |
| FLU 1458-21 | 125D +127E | V216I | 1X10$^7$ |
| FLU 1459-25 | 125D +127E | L249V | 1X10$^7$ |
| FLU 1460-42 | 125D +127E | E283K | 1X10$^7$ |
|  | 125D +127E | K119E | Virus not rescued |

SEQUENCE LISTING

```
<160> NUMBER OF SEQ ID NOS: 32

<210> SEQ ID NO 1
<211> LENGTH: 549
<212> TYPE: PRT
<213> ORGANISM: Influenza A virus

<400> SEQUENCE: 1

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30
```

```
Leu Glu Asp Lys His Asn Gly Lys Leu Cys Lys Leu Arg Gly Val Ala
         35                  40                  45

Pro Leu His Leu Gly Lys Cys Asn Ile Ala Gly Trp Ile Leu Gly Asn
 50                  55                  60

Pro Glu Cys Glu Ser Leu Ser Thr Ala Ser Ser Trp Ser Tyr Ile Val
 65                  70                  75                  80

Glu Thr Ser Ser Ser Asp Asn Gly Thr Cys Tyr Pro Gly Asp Phe Ile
                 85                  90                  95

Asn Tyr Glu Glu Leu Arg Glu Gln Leu Ser Ser Val Ser Ser Phe Glu
                100                 105                 110

Arg Phe Glu Ile Phe Pro Lys Thr Ser Ser Trp Pro Asn His Asp Ser
            115                 120                 125

Asn Lys Gly Val Thr Ala Ala Cys Pro His Ala Gly Ala Lys Ser Phe
130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Thr Ser Lys Tyr Ser Lys
        195                 200                 205

Lys Phe Lys Pro Glu Ile Ala Val Arg Pro Lys Val Arg Asp Gln Glu
210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Leu Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Glu Gly Ala Ile Asn Thr
        275                 280                 285

Ser Leu Pro Phe Gln Asn Ile His Pro Ile Thr Leu Gly Lys Cys Pro
    290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Lys Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445
```

-continued

```
Val Arg Ser Gln Leu Lys Asn Asn Ala Lys Glu Ile Gly Asn Gly Cys
    450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Glu Ile Asp Gly Val Lys Leu Glu Ser Thr Arg Ile Tyr Gln
            500                 505                 510

Ile Leu Ala Ile Tyr Ser Thr Val Ala Ser Ser Leu Val Leu Val Val
        515                 520                 525

Ser Leu Gly Ala Ile Ser Phe Trp Met Cys Ser Asn Gly Ser Leu Gln
    530                 535                 540

Cys Arg Ile Cys Ile
545
```

<210> SEQ ID NO 2
<211> LENGTH: 1701
<212> TYPE: DNA
<213> ORGANISM: Influenza A virus

<400> SEQUENCE: 2

```
gtgaaggcaa tactagtagt tctgctatat acatttgcaa ccgcaaatgc agacacatta      60
tgtataggtt atcatgcgaa caattcaaca gacactgtag acacagtact agaaaagaat     120
gtaacagtaa cacactctgt taaccttcta gaagacaagc ataacgggaa attatgcaaa     180
ctaagagggg tagccccatt gcatttgggt aaatgtaaca ttgctggctg gatcctggga     240
aatccagagt gtgaatcact ctccacagca agctcatggt cctacattgt ggaaacatct     300
agttcagaca atggaacgtg ttacccagga gatttcatcg attatgagga gctaagagaa     360
caattgagct cagtgtcatc atttgaaagg tttgagatat tccccaagac aagttcatgg     420
cccgatcatg amtcgaacaa aggtgtaacg gcagcatgtc ctcatgctgg agcaaaaagc     480
ttctacaaaa atttaatatg gctagttaaa aaaggaaatt catacccaaa gctcagcaaa     540
tcctacatta atgataaagg gaaagaagtc ctcgtgctat ggggcattca ccatccatct     600
actagtgctg accaacaaag tctctatcag aatgcagatg catatgtttt tgtggggaca     660
tcaagataca gcaagaagtt caagccggaa atagcaataa gacccaaagt gagggatcaa     720
gaagggagaa tgaactatta ctggacacta gtagagccgg gagacaaaat aacattcgaa     780
gcaactggaa atctagtggt accgagatat gcattcgcaa tggaaagaaa tgctggatct     840
ggtattatca tttcagatac accagtccac gattgcaata caacttgtca gacacccaag     900
ggtgctataa acaccagcct cccatttcag aatatacatc cgatcacaat tggaaaatgt     960
ccaaaatatg taaaaagcac aaaattgaga ctggccacag gattgaggaa tgtcccgtct    1020
attcaatcta gaggcctatt tggggccatt gccggtttca ttgaaggggg gtggacaggg    1080
atggtagatg gatggtacgg ttatcaccat caaaatgagc aggggtcagg atatgcagcc    1140
gacctgaaga gcacacagaa tgccattgac aagattacta acaaagtaaa ttctgttatt    1200
gaaaagatga atacacagtt cacagcagta ggtaaagagt tcaaccacct ggaaaaaaga    1260
atagagaatt taaataaaaa agttgatgat ggtttcctgg acatttggac ttacaatgcc    1320
gaactgttgg ttctattgga aaatgaaaga actttggact accacgattc aaatgtgaag    1380
aacttatatg aaaaggtaag aagccagtta aaaaacaatg ccaaggaaat tggaaacggc    1440
tgctttgaat tttaccacaa atgcgataac acgtgcatgg aaagtgtcaa aaatgggact    1500
```

```
tatgactacc caaaatactc agaggaagca aaattaaaca gagaagaaat agatggggta    1560
aagctggaat caacaaggat ttaccagatt ttggcgatct attcaactgt cgccagttca    1620
ttggtactgg tagtctccct gggggcaatc agtttctgga tgtgctctaa tgggtctcta    1680
cagtgtagaa tatgtattta a                                              1701

<210> SEQ ID NO 3
<211> LENGTH: 469
<212> TYPE: PRT
<213> ORGANISM: Influenza A virus

<400> SEQUENCE: 3

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Ser Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Ile Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Ser Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335
```

```
Pro Val Ser Ser Asn Gly Ala Asn Gly Val Lys Gly Phe Ser Phe Lys
                340                 345                 350

Tyr Gly Asn Gly Val Trp Ile Gly Arg Thr Lys Ser Ile Ser Ser Arg
            355                 360                 365

Lys Gly Phe Glu Met Ile Trp Asp Pro Asn Gly Trp Thr Gly Thr Asp
        370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Met Ser Phe Cys Gly Val
        435                 440                 445

Asn Ser Asp Thr Val Gly Trp Ser Trp Pro Asp Gly Ala Glu Leu Pro
450                 455                 460

Phe Thr Ile Asp Lys
465

<210> SEQ ID NO 4
<211> LENGTH: 1410
<212> TYPE: DNA
<213> ORGANISM: Influenza A virus

<400> SEQUENCE: 4
atgaatccaa accaaaagat aataaccatt ggttcggtct gtataacaat tggaatggct        60
aacttaatat acaaattgg aaacataatc tcaatatgga ttagccactc aattcaactt       120
gggaatcaaa atcagattga acatgcaat caaagcgtca ttacttatga aaacaacact       180
tgggtaaatc agacatatgt taacatcagc aacaccaact tgctgctgg acagtcagtg       240 gtttccgtga aattagcggg caattcctct ctctgcccctg ttagtggatg gctatatac       300 agtaaagaca acagtataag aatcggttcc aaggggatg tgtttgtcat aagggaacca       360
ttcatatcat gctccccctt ggaatgcaga accttcttct tgactcaagg ggccttgcta       420
aatgacaaac attccaatgg aaccattaaa gacaggagcc catatcgaac cctaatgagc       480
tgtcctattg gtgaagttcc ctctccatac aactcaagat tgagtcagt cgcttggtca       540 gcaagtgctt gtcatgatgg catcagttgg ctaacaattg aatttctggg cccagacaat       600
ggggcagtgg ctgtgttaaa gtacaacggc ataataacag acactatcaa gagttggaga       660
aacaatatat tgagaacaca agagtctgaa tgtgcatgtg taaatggttc ttgtttact       720 gtaatgaccg atggaccaag tgatggacag gcctcataca agatcttcag aatagaaaag       780
ggaaagatag tcaaatcagt cgaaatgaat gcccctaatt atcactatga ggaatgctcc       840
tgttatcctg attctagtga aatcacatgt gtgtgcaggg ataactggca tggctcgaat       900
cgaccgtggg tgtctttcaa ccagaatctg gaatatcaga taggatacat atgcagtggg       960 atttttcggag acaatccacg ccctaatgat aagacaggca gttgtggtcc agtatcgtct      1020
aatggagcaa atggagtaaa aggattttca ttcaaatacg gcaatggtgt ttggataggg      1080
agaactaaaa gcattagttc aagaaacggt tttgagatga tttgggatcc gaacggatgg      1140
actgggacag acaataactt ctcaataaag caagatatcg taggaataaa tgagtggtca      1200
ggatatagcg ggagttttgt tcagcatcca gaactaacag gctggattg tataaaacct      1260 tgcttctggg ttgaactaat cagagggcga cccaagagaa acacaatctg gactagcggg      1320
```

```
agcagcatat cctttgtgg tgtaaacagt gacactgtgg gttggtcttg gccagacggt    1380
gctgagttgc catttaccat tgacaagtaa                                    1410
```

<210> SEQ ID NO 5
<211> LENGTH: 549
<212> TYPE: PRT
<213> ORGANISM: Influenza A virus
<220> FEATURE:
<221> NAME/KEY: MOD_RES
<222> LOCATION: (127)..(127)
<223> OTHER INFORMATION: Any amino acid

<400> SEQUENCE: 5

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Ser Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asp His Xaa Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Thr Ser Arg Tyr Ser Lys
        195                 200                 205

Lys Phe Lys Pro Glu Ile Ala Ile Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                325                 330                 335
```

-continued

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Lys Ile Thr Asn Lys Val Asn Ser Val Ile Glu
370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
            405                 410                 415

Asp Ile Trp Thr Tyr Asn Ala Glu Leu Leu Val Leu Leu Glu Asn Glu
        420                 425                 430

Arg Thr Leu Asp Tyr His Asp Ser Asn Val Lys Asn Leu Tyr Glu Lys
    435                 440                 445

Val Arg Ser Gln Leu Lys Asn Asn Ala Lys Glu Ile Gly Asn Gly Cys
450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
            485                 490                 495

Arg Glu Glu Ile Asp Gly Val Lys Leu Glu Ser Thr Arg Ile Tyr Gln
        500                 505                 510

Ile Leu Ala Ile Tyr Ser Thr Val Ala Ser Ser Leu Val Leu Val Val
    515                 520                 525

Ser Leu Gly Ala Ile Ser Phe Trp Met Cys Ser Asn Gly Ser Leu Gln
530                 535                 540

Cys Arg Ile Cys Ile
545

<210> SEQ ID NO 6
<211> LENGTH: 469
<212> TYPE: PRT
<213> ORGANISM: Influenza A virus

<400> SEQUENCE: 6

Met Asn Pro Asn Gln Lys Ile Ile Thr Ile Gly Ser Val Cys Ile Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Ile Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

```
Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Ser Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asp Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Lys Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 7
<211> LENGTH: 549
<212> TYPE: PRT
<213> ORGANISM: Influenza A virus

<400> SEQUENCE: 7

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60
```

-continued

```
Pro Glu Cys Glu Ser Leu Ser Thr Ala Ser Ser Trp Ser Tyr Ile Val
 65                  70                  75                  80

Glu Thr Pro Ser Ser Asp Asn Gly Thr Cys Tyr Pro Gly Asp Phe Ile
                 85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Lys
        195                 200                 205

Lys Phe Lys Pro Glu Ile Ala Ile Arg Pro Lys Val Arg Gly Gln Glu
210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Glu Ile Thr Asn Lys Val Asn Ser Val Ile Glu
370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Ser Gln Leu Lys Asn Asn Ala Lys Glu Ile Gly Asn Gly Cys
450                 455                 460

Phe Glu Phe Tyr His Lys Cys Asp Asn Thr Cys Met Glu Ser Val Lys
465                 470                 475                 480
```

```
Asn Gly Thr Tyr Asp Tyr Pro Lys Tyr Ser Glu Glu Ala Lys Leu Asn
            485                 490                 495

Arg Glu Glu Ile Asp Gly Val Lys Leu Glu Ser Thr Arg Ile Tyr Gln
            500                 505                 510

Ile Leu Ala Ile Tyr Ser Thr Val Ala Ser Ser Leu Val Leu Val Val
            515                 520                 525

Ser Leu Gly Ala Ile Ser Phe Trp Met Cys Ser Asn Gly Ser Leu Gln
            530                 535                 540

Cys Arg Ile Cys Ile
545

<210> SEQ ID NO 8
<211> LENGTH: 469
<212> TYPE: PRT
<213> ORGANISM: Influenza A virus

<400> SEQUENCE: 8

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300
```

```
Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tattcgtctc agggagcaaa agcaggggaa                                     30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tattcgtctc agggagcaaa agcagggaa                                      30

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atatcgtctc gtattagtag aaacaagggt gttttt                              36

<210> SEQ ID NO 12
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 12
tattcgtctc agggagcaaa agcaggagt                                        29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tattcgtctc agggagcaaa agcaggagt                                        29

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tattcgtctc agggagtaga aacaaggagt tttt                                  34

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
taactagaga acccactgct tactggc                                          27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcgctccgt gtgtggctgc gatggtg                                          27

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccaagacaa gttcatggcc                                                  20

<210> SEQ ID NO 18
<211> LENGTH: 35
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 18
gacaagttca tggcccgatc atgactcgaa caaag                              35

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctttgttcga gtcatgatcg ggccatgaac ttgtc                              35

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
catggcccaa tcatgaatcg aacaaaggtg taacg                              35

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgttacacct ttgttcgatt catgattggg ccatg                              35

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gacaagttca tggcccgatc atgaatcgaa caaaggtg                           38

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cacctttgtt cgattcatga tcgggccatg aacttgtc                           38

<210> SEQ ID NO 24
<211> LENGTH: 38
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 24
gacaagttca tggcccgaac atgaatcgaa caaaggtg                              38

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cacctttgtt cgattcatgt tcgggccatg aacttgtc                              38

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gacaagttca tggcccgaac atgactcgaa caaag                                 35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctttgttcga gtcatgttcg ggccatgaac ttgtc                                 35

<210> SEQ ID NO 28
<211> LENGTH: 566
<212> TYPE: PRT
<213> ORGANISM: Influenza A virus

<400> SEQUENCE: 28
```

Met Lys Ala Ile Leu Val Val Leu Leu Tyr Thr Phe Ala Ile Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

-continued

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Lys Tyr Ser
210                 215                 220

Lys Lys Phe Lys Pro Glu Ile Ala Val Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Leu Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Glu Gly Ala Ile Asn
290                 295                 300

Thr Ser Leu Pro Phe Gln Asn Ile His Pro Ile Thr Leu Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
530                 535                 540

-continued

```
Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 29
<211> LENGTH: 566
<212> TYPE: PRT
<213> ORGANISM: Influenza A virus
<220> FEATURE:
<221> NAME/KEY: MOD_RES
<222> LOCATION: (144)..(144)
<223> OTHER INFORMATION: Any amino acid

<400> SEQUENCE: 29

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asp His Xaa
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320
```

```
Pro Lys Tyr Val Lys Ser Thr Lys Leu Arg Leu Ala Thr Gly Leu Arg
            325                 330                 335

Asn Val Pro Ser Ile Gln Ser Arg Gly Leu Phe Gly Ala Ile Ala Gly
        340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
        370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
            405                 410                 415

Leu Glu Lys Arg Ile Glu Asn Leu Asn Lys Lys Val Asp Asp Gly Phe
        420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
        450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
            485                 490                 495

Lys Asn Gly Thr Tyr Asp Tyr Pro Lys Tyr Ser Glu Glu Ala Lys Leu
        500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 30
<211> LENGTH: 566
<212> TYPE: PRT
<213> ORGANISM: Influenza A virus

<400> SEQUENCE: 30

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
            85                  90                  95

Val Glu Thr Pro Ser Ser Asp Asn Gly Thr Cys Tyr Pro Gly Asp Phe
        100                 105                 110

Ile Asp Tyr Glu Glu Leu Arg Glu Gln Leu Ser Ser Val Ser Ser Phe
        115                 120                 125
```

```
Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
210                 215                 220

Lys Lys Phe Lys Pro Glu Ile Ala Ile Arg Pro Lys Val Arg Gly Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
530                 535                 540
```

```
Val Ser Leu Gly Ala Ile Ser Phe Trp Met Cys Ser Asn Gly Ser Leu
545                 550                 555                 560

Gln Cys Arg Ile Cys Ile
            565
```

<210> SEQ ID NO 31
<211> LENGTH: 4
<212> TYPE: PRT
<213> ORGANISM: Influenza A virus

<400> SEQUENCE: 31

```
Arg Arg Lys Lys
1
```

<210> SEQ ID NO 32
<211> LENGTH: 566
<212> TYPE: PRT
<213> ORGANISM: Artificial Sequence
<220> FEATURE:
<223> OTHER INFORMATION: Description of Artificial Sequence: Synthetic
      consensus polypeptide

<400> SEQUENCE: 32

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270
```

-continued

```
Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

SWINE INFLUENZA HEMAGGLUTININ VARIANTS

RELATED PATENT APPLICATION

This patent application claims the benefit of U.S. Provisional Application No. 61/545,055 filed on Oct. 7, 2011, entitled SWINE INFLUENZA HEMAGGLUTININ VARIANTS, naming Hong Jin and Zhongying Chen as inventors. The entirety of the foregoing provisional patent application is incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 13, 2012, is named MDI109UT.txt and is 55,121 bytes in size.

FIELD

The technology relates in part to modified influenza viruses useful for vaccine development.

BACKGROUND

The global spread of swine-origin influenza A (H1N1) viruses in humans in April 2009 marked the first influenza pandemic in 41 years. Over 35,000 people were infected with this novel H1N1 virus as of Jun. 15, 2009. Last century, an H1N1 influenza virus also caused the devastating 1918-19 pandemic. In addition, an H1N1 virus derived from swine caused an abortive pandemic in 1976. The 1918 influenza virus caused an influenza outbreak in the spring of 1918 and a lethal wave globally in the fall of that year, killing as many as 50 million people worldwide. Although the 2009 swine-origin H1N1 influenza virus was viewed as mild in early 2009, the possibility exists that this virus may mutate and become more virulent in the future. Thus, there is a need to develop effective vaccines to prevent future outbreaks caused by H1N1 viruses.

SUMMARY

Provided in some aspects are reassortant influenza viruses comprising a first genome segment encoding a modified hemagglutinin polypeptide where (a) the amino acid at position 125, or a position corresponding to residue 125 of SEQ ID NO:1, is substituted with a non-native amino acid, and/or (b) the amino acid at position 127, or a position corresponding to residue 127 of SEQ ID NO:1, is substituted with a non-native amino acid.

Also provided are methods for increasing the peak titer in embryonated eggs for a reassortant or recombinant influenza virus comprising a hemagglutinin polypeptide, comprising substituting one or more amino acid residues of the hemagglutinin polypeptide at position 125, or a residue corresponding to position 125 of SEQ ID NO:1, and/or at position 127, or a residue corresponding to position 127 of SEQ ID NO:1, with non-native amino acid residues, thereby increasing the peak titer in embryonated eggs for the influenza virus. In some aspects, the peak titer in embryonated eggs for the reassortant or recombinant influenza virus is increased at least 1.5-fold, 2-fold, 4-fold or 10-fold relative to the same reassortant or recombinant influenza virus not comprising the one or more amino acid substitutions.

Also provided are isolated or recombinant modified hemagglutinin polypeptides, or fragments thereof, where, (a) the amino acid at position 125, or a position corresponding to residue 125 of SEQ ID NO:1, is substituted with a non-native amino acid, and/or (b) the amino acid at position 127, or a position corresponding to residue 127 of SEQ ID NO:1, is substituted with a non-native amino acid.

In some aspects, the non-native amino acid is an acidic side-chain amino acid. In some aspects, the unmodified hemagglutinin polypeptide comprises the amino acid sequence of SEQ ID NO:1 or SEQ ID NO:7, or a fragment thereof. In some aspects, the amino acid sequence comprises amino acids 1-327 of SEQ ID NO:1 or SEQ ID NO:7. In some aspects, the amino acid at position 125 is substituted with an aspartic acid (D) or a glutamic acid (E). In some aspects, the amino acid at position 127 is substituted with a glutamic acid (E). In some aspects, the amino acid at position 125 is substituted with an aspartic acid (D) and the amino acid at position 127 is substituted with a glutamic acid (E). In some aspects, the amino acid at position 125 is substituted with a glutamic acid (E) and the amino acid at position 127 is substituted with a glutamic acid (E).

In some aspects, the reassortant virus is a 6:2 reassortant virus comprising 6 internal genome segments from one or more donor viruses and a second genome segment encoding a neuraminidase polypeptide. In some cases, the neuraminidase polypeptide is a swine influenza virus neuraminidase and sometimes is an N1 neuraminidase. In some cases, the neuraminidase polypeptide comprises the amino acid sequence of SEQ ID NO:3 or SEQ ID NO:8, or a fragment thereof. In some cases, the neuraminidase polypeptide comprises the amino acid sequence of SEQ ID NO:6, or a fragment thereof. In some aspects, the reassortant virus is a 7:1 reassortant virus comprising 6 internal genome segments and a second genome segment encoding a neuraminidase polypeptide from one or more donor viruses. In some cases, the donor virus comprises one or more phenotypic attributes selected from the group consisting of: attenuated, cold-adapted, and temperature-sensitive. In some cases, the donor virus is selected from the group consisting of: A/Ann Arbor/6/60, A/Puerto Rico/8/34, A/Leningrad/134/17/57, and A/Leningrad/17. In some aspects, the virus is a live virus.

Also provided are immunogenic compositions comprising any of the above reassortant influenza viruses or polypeptides. Also provided is an influenza vaccine comprising any of the above reassortant influenza viruses or polypeptides. Also provided is a live, cold-adapted, temperature-sensitive, attenuated influenza vaccine comprising any of the above reassortant influenza viruses or polypeptides. Also provided are isolated or recombinant nucleic acids comprising nucleotide sequences encoding any of the above polypeptides Certain aspects are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A and FIG. 1B show structural features of the HA protein. Residues that differ between Gilroy11 and Brisbane10 are labeled and indicated with arrows. In FIG. 1A, residues 125 and 127 (of a mature HA protein) are on the top of the HA protein (i.e. HA head region). Residues 216, 205 and 283 are on the interface of the HA trimer. Residues 97N, 249L and 300L are embedded in the HA protein. FIG. 1B shows modeling of the HA protein and amino acid charges with wild-type amino acids 125N/127D and substituted amino acids 125D/127E on the HA head region.

In FIG. 2A, viral RNA was amplified by RT-PCR using HA and NA specific primers and template RNA from virus grown in eggs and MDCK cells. The cDNAs were run on a 1% agarose gel and EtBr-stained DNA bands were photographed. In FIG. 2B, HA cDNA and NA cDNA cloned into the pAD3000 vector were digested by restriction enzymes and confirmed to have the expected pattern.

In FIG. 3A, the viruses amplified in eggs were titrated by plaque assay and their titers were graphed. The virus without HA amino acid changes had a titer of less than 4 logs. The three variants had comparable titers. In FIG. 3B, the viruses with double substitutions (i.e. N125D/D127E and N125E/D127E) had larger plaques compared to the virus with a single substitution at position 127 (i.e. D127E). Gilroy11 viruses grown in eggs had an I at position 191 in the HA amino acid sequence and Gilroy11 viruses grown in MDCK cells had an L at position 191 in the HA amino acid sequence.

FIG. 4 presents the amino acid sequence (including the signal peptide sequence) for the full-length HA protein of the A/Gilroy/231/2011 virus (SEQ ID NO:28).

FIG. 5 presents the nucleic acid sequence which encodes the full-length HA protein of the A/Gilroy/231/2011 virus (SEQ ID NO:2).

FIG. 6 presents the amino acid sequence for the full-length NA protein of the A/Gilroy/231/2011 virus (SEQ ID NO:3).

FIG. 7 presents the nucleic acid sequence which encodes the full-length NA protein of the A/Gilroy/231/2011 virus (SEQ ID NO:4).

FIG. 8 shows a comparison of full-length HA amino acid sequences of three H1N1 viruses: A/Brisbane/10/10 (SEQ ID NO:29), A/California/04/09 (SEQ ID NO:30), and A/Gilroy/231/11 (SEQ ID NO:28). Residues at positions 125 and 127 of the mature H1 polypeptide for A/Brisbane/10/10 are underlined and in bold.

FIG. 9 shows a comparison of NA amino acid sequences of three H1N1 viruses: A/Brisbane/10/10 (SEQ ID NO:6), A/California/04/09 (SEQ ID NO:8), and A/Gilroy/231/11 (SEQ ID NO:3).

FIGS. 10A and 10B shows a comparison of HA amino acid sequences of three H1N1 viruses: A/Brisbane/10/10 (SEQ ID NO:29), A/California/04/09 (SEQ ID NO:30), and A/Gilroy/231/11 (SEQ ID NO:28). Residues at positions 125 and 127 of the mature H1 polypeptide for all three viruses are outlined with a rectangle. Other amino acid differences throughout the sequences are circled. The residue at position 127 of the mature A/Brisbane/10/10 HA is represented by an "X", because the amino acid sequence contained D at position 127 in some cases and E at position 127 in some cases. FIGS. 10A and 10B disclose the consensus sequence as SEQ ID NO: 32.

FIG. 11 shows virus titers and plaque images for various reassortant viruses as indicated.

FIG. 12 shows comparison of pH1N1 virus titers by different methods. Virus titers for the A/Gilroy/2011 HA (N125D/D127E) reassortant and A/Gilroy/2011 HA (N125D/D127E) with A/Brisbane/2010 NA reassortant are outlined.

FIG. 13 shows growth titers for reassortants with additional amino acid changes in the HA of A/Gilroy/231/2011. The reassortant with a modified A/Gilroy/2011 HA (N125D/D127E/K119E) was not recovered.

DETAILED DESCRIPTION

Figure 2A:
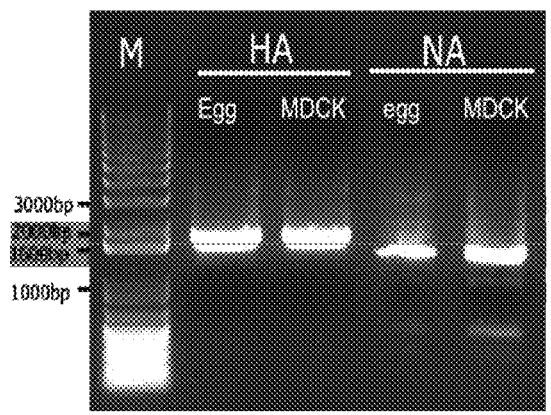
FIG. 2A and FIG. 2B show electrophoresis images for HA and NA cDNA cloning steps.

6:2 reassortant influenza viruses, having the HA and NA segments of swine-origin influenza A (H1N1) viruses and the "backbone" segments of attenuated influenza viruses, can be constructed for the development of both live and killed (i.e. inactivated) vaccines. However, many influenza strains display low titers in eggs. Certain isolates also infect MDCK cells poorly and form tiny plaques with poor cytopathic effect (CPE). In some cases, a severe loss of virus potency is observed after virus filtration. Thus, certain H1N1 reassortant influenza virus strains are poor candidates for the development of vaccines. Provided herein are new swine influenza H1 hemagglutinin variants that are useful for the production of numerous types of vaccines. Such hemagglutinin variants also can be useful for research, diagnostics, and the like. Further provided herein are methods for improving the replication efficiency of H1 influenza viruses.

Influenza Virus

The polypeptides and polynucleotides provided in some embodiments are variants of influenza HA and/or NA sequences. Influenza viruses are typically made up of an internal ribonucleoprotein core containing a segmented single-stranded RNA genome and an outer lipoprotein envelope lined by a matrix protein. The genome of influenza viruses is composed of eight segments of linear (−) strand ribonucleic acid (RNA), encoding immunogenic hemagglutinin (HA) and neuraminidase (NA) proteins, and six internal core polypeptides: a nucleocapsid nucleoprotein (NP); matrix proteins (M); non-structural proteins (NS); and 3 RNA polymerase (PA, PB1, PB2) proteins. During replication, genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, a nucleocapsid nucleoprotein (NP) and a polymerase complex (PB1, PB2, and PA). The hemagglutinin molecule includes a surface glycoprotein and can bind to N-AcetylNeuraminic acid (NeuNAc), also known as sialic acid, on host cell surface receptors. Hemagglutinin is made up of two subunits, HA1 and HA2 and the entire structure is about 550 amino acids in length and about 220 kD. Neuraminidase molecules cleave terminal sialic acid residues from cell surface receptors of the influenza virus, thereby releasing virions from infected cells. Neuraminidase also removes sialic acid from newly made hemagglutinin and neuraminidase molecules.

Influenza is typically grouped into influenza A and influenza B categories, and sometimes a less common C category. Influenza A and influenza B viruses each contain eight segments of single stranded RNA with negative polarity. The influenza A genome encodes eleven polypeptides. Segments 1-3 encode three polypeptides, making up an RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants. The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a bicistronic mRNA. Segment 7 of influenza B also encodes two proteins: M1 and BM2. The smallest segment encodes two products: NS1 is translated from the full length RNA, while NS2 is translated from a spliced mRNA variant.

Influenza types A and B are typically associated with influenza outbreaks in human populations. However, type A influenza also infects other species as well, e.g., birds, pigs, and other animals. The type A viruses are categorized into subtypes based upon differences within their hemagglutinin and neuraminidase surface glycoprotein antigens. Hemagglutinin in type A viruses has 16 known subtypes and neuraminidase has 9 known subtypes. In humans, currently only about 4 different hemagglutinin and 2 different neuraminidase subtypes are known, e.g., H1, H2, H3, H5, N1, and N2. In particular, two major subtypes of influenza A have been active in humans, namely, H1N1 and H3N2. H1N2, however has recently been of concern. Influenza B viruses typically are not divided into subtypes based upon their hemagglutinin and neuraminidase proteins.

Different strains of influenza can be categorized based upon, e.g., the ability of influenza to agglutinate red blood cells (RBCs or erythrocytes). Antibodies specific for particular influenza strains can bind to the virus and, thus, prevent such agglutination. Assays determining strain types based on such inhibition are typically known as hemagglutinin inhibition assays (HI assays or HAI assays) and are standard and well known methods in the art to characterize influenza strains. Other assays including, for example, ELISA, indirect fluorescent antibody assays, immunohistochemistry, Western blot assays, and the like, can be used to characterize influenza strains and the use of and discussion herein of HI assays should not be necessarily construed as limiting.

Briefly, in typical HI assays, sera to be used for typing or categorization, which is often produced in ferrets, is added to erythrocyte samples in various dilutions, e.g., 2-fold, and the like. Optical determination is then made whether the erythrocytes are clumped together (i.e., agglutinated) or are suspended (i.e., non-agglutinated). If the cells are not clumped, then agglutination did not occur due to the inhibition from antibodies in the sera that are specific for that influenza. Thus, the types of influenza are defined as being within the same strain. In some cases, one strain is described as being "like" the other, e.g., strain x is a "y-like" strain. For example, if two samples are within four-fold titer of one another as measured by an HI assay, then they can be described as belonging to the same strain (e.g., both belonging to the "New Caledonia" strain or both being "Moscow-like" strains). In other words, strains are typically categorized based upon their immunologic or antigenic profile. An HAI titer is typically defined as the highest dilution of a serum that completely inhibits hemagglutination. See, e.g., Schild, et al., Bull. Wld. Hlth. Org. (1973) 48:269-278.

From the above it will be appreciated that the polypeptides provided herein (and nucleic acids encoding the polypeptides provided herein) not only include the specific sequences listed herein, but also such sequences within various vectors (e.g., those used for plasmid reassortment and rescue, described in further detail below) as well as hemagglutinin and neuraminidase sequences within the same strains as the sequences listed herein. Also, such same strains that are within various vectors (e.g., typically ones used for plasmid reassortment and rescue such as A/Ann Arbor/6/60 or B/Ann Arbor/1/66, A/Puerto Rico/8/34, B/Leningrad/14/17/55, B/14/5/1, B/USSR/60/69, B/Leningrad/179/86, B/Leningrad/14/55, or B/England/2608/76, and the like) are also included.

As used herein, the term "similar strain" should be taken to indicate that a first influenza virus is of the same or related strain as a second influenza virus. In typical embodiments such relation is commonly determined through use of an HAI assay. Influenza viruses that fall within a four-fold titer of one another in an HAI assay are, thus, of a "similar strain." Other assays are known in the art for the determination of similar strains, e.g., FRID, neutralization assays, and the like. The polypeptides provided herein (and the nucleic acids that encode the polypeptides provided herein) also comprise such similar strains in the various plasmids, vectors, viruses, methods, and the like herein. Thus, unless the context clearly dictates otherwise, descriptions herein of particular sequences (e.g., those in the sequence listing) or fragments thereof also should be considered to include sequences from similar strains to those (i.e., similar strains to those strains having the sequences in those plasmids, vectors, viruses, and the like herein). Also, it will be appreciated that the NA and HA polypeptides within such similar strains are, thus, "similar polypeptides" when compared between "similar strains."

Influenza Virus Vaccines

The sequences, compositions and methods herein are useful for the production of influenza viruses for vaccines, in some embodiments. Often, influenza virus vaccines are produced in embryonated hen eggs using strains of virus selected or based on empirical predictions of relevant strains. In some cases, reassortant viruses can be produced that incorporate selected hemagglutinin and/or neuraminidase antigens in the context of an approved attenuated, temperature sensitive master strain. Following culture of the virus through multiple passages in hen eggs, influenza viruses can be recovered and, optionally, inactivated, e.g., using formaldehyde and/or β-propiolactone. In some cases, live attenuated vaccines are produced. Thus, it will be appreciated that HA and NA sequences, such as those provided herein, are quite useful in constructing influenza vaccines.

Reassortant viruses can be referred to herein as a chimeric viruses or recombinant viruses. The term "chimeric" or "chimera," when referring to a virus, indicates that the virus includes genetic and/or polypeptide components derived from more than one parental viral strain or source. Similarly, the term "chimeric" or "chimera," when referring to a viral protein, indicates that the protein includes polypeptide components (i.e., amino acid subsequences) derived from more than one parental viral strain or source. As will be apparent herein, such chimeric viruses are typically reassortant/recombinant viruses. Thus, in some embodiments, a chimera can include, for example, a sequence (e.g., of HA and/or NA) from an A influenza virus placed into a backbone comprised of, or constructed/derived from a B influenza virus (e.g., B/AA/1/66) or a B influenza virus sequence placed into an A influenza virus backbone (i.e., donor virus) such as, e.g., A/AA/6/60.

The term "recombinant" indicates that the material (e.g., a nucleic acid or protein) has been artificially or synthetically (non-naturally) altered by human intervention. The alteration can be performed on the material within, or removed from, its natural environment or state. Specifically, e.g., an influenza virus is recombinant when it is produced by the expression of a recombinant nucleic acid. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

The term "reassortant," when referring to a virus (typically herein, an influenza virus), indicates that the virus includes genetic and/or polypeptide components derived from more than one parental viral strain or source. For example, a 7:1 reassortant includes 7 viral genome segments (or gene segments) derived from a first parental virus, and a single complementary viral genome segment, e.g., encoding a hemagglutinin or neuraminidase described herein. A 6:2 reassortant includes 6 genome segments, most commonly the 6 internal genome segments from a first parental virus, and two complementary segments, e.g., hemagglutinin and neuraminidase genome segments, from one or more different parental virus. As mentioned above, reassortant viruses also can, depending upon context herein, be termed as "chimeric" and/or "recombinant."

In some cases, recombinant and reassortant vaccines are produced in cell culture using a vector system (see, e.g., U.S. Pat. No. 8,012,736 and U.S. application Ser. No. 12/254,131). Such systems can be useful for rapid production vaccines corresponding to one or many selected antigenic strains of virus, e.g., either A or B strains, various subtypes or substrains, and the like, e.g., comprising the HA and NA sequences herein. Typically, cultures are maintained in a system, such as a cell culture incubator, under controlled humidity and $CO_2$, at constant temperature using a temperature regulator, such as a thermostat to insure that the temperature does not exceed 35° C. Reassortant influenza viruses can be readily obtained by introducing a subset of vectors corresponding to genomic segments of a master influenza virus, in combination with complementary segments derived from strains of interest (e.g., HA and NA antigenic variants herein). Typically, master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. As explained elsewhere herein and, e.g., in U.S. Pat. No. 8,012,736, various embodiments herein utilize A/Ann Arbor (AA)/6/60 or B/Ann Arbor/1/66 or A/Puerto Rico/8/34, or B/Leningrad/14/17/55, B/14/5/1, B/USSR/60/69, B/Leningrad/179/86, B/Leningrad/14/55, or B/England/2608/76 influenza strain as a "backbone" upon which to add HA and/or NA genes (e.g., such as sequences listed herein and variants thereof) to create desired reassortant viruses. Thus, for example, in a 6:2 reassortant, 2 genes (i.e., NA and HA) would be from the influenza strain(s) against which an immunogenic reaction is desired, while the other 6 genes would be from the Ann Arbor strain, or other backbone strain. The Ann Arbor virus is useful for its cold adapted, attenuated, temperature sensitive attributes. Additionally, the HA and NA sequences and variants thereof provided herein are capable of reassortment with a number of other virus genes or virus types (e.g., a number of different "backbones" such as A/Puerto Rico/8/34, for example, containing other influenza genes present in a reassortant, namely, the non-HA and non-NA genes). In some embodiments, the reassortants can be 7:1 reassortants. In such cases, either the HA or the NA is from a different strain than the backbone or MDV strain.

In some embodiments, the sequences herein can optionally have specific regions removed (both or either in the nucleic acid sequence or the amino acid sequence). For example, for those molecules having a polybasic cleavage site, such sites can optionally be removed. Such cleavage sites, in some embodiments, can be modified or altered in their sequences in comparison to the wild-type sequences from which such sequences are derived (e.g., to disable the cleavage or reduce the cleavage). Such modifications/alterations can be different in different strains or sequences due to the various sequences of the cleavage sites in the starting sequences. For example, 4 polybasic residues (RRKK (SEQ ID NO: 31)) are typically removed in some HA sequences. In various embodiments, such polybasic cleavage sites can be modified in a number of ways, all of which are contemplated herein. For example, the polybasic cleavage site can be removed one amino acid at a time (e.g., one R removed, two Rs removed, RRK removed, or RRKK (SEQ ID NO: 31) removed). Additionally, an amino acid residue directly upstream of the cleavage site also can be removed or altered (e.g., from an R to a T). The nucleotides encoding the amino acid residue directly after the cleavage site also can be modified. The resulting shortened sequences also are contemplated herein.

In some embodiments, viruses are temperature sensitive, cold adapted and/or attenuated. The terms "temperature sensitive", "cold adapted" and "attenuated" as applied to viruses (typically used as vaccines or for vaccine production) are known in the art. For example, the term "temperature sensitive" (ts) indicates, for example, that a virus exhibits a 100 fold or greater reduction in titer at 39° C. relative to 33° C. for influenza A strains, or that the virus exhibits a 100 fold or greater reduction in titer at 37° C. relative to 33° C. for influenza B strains. The term "cold adapted" (ca) indicates that the virus exhibits growth at 25° C. within 100 fold of its growth at 33° C., while the term "attenuated" (att) indicates that the virus replicates in the upper airways of ferrets but is not detectable in their lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), or exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses and can be used in conjunction with the HA and NA sequences herein.

Thus, methods described herein can utilize growth, e.g., in appropriate culture conditions, of virus strains (both A strain and B strain influenza viruses) with desirable properties relative to vaccine production (e.g., attenuated pathogenicity or phenotype, cold adaptation, temperature sensitivity, and the like) in vitro in cultured cells. Influenza viruses can be produced by introducing a plurality of vectors incorporating cloned viral genome segments into host cells, and culturing the cells at a temperature not exceeding 35° C., for example. When vectors including an influenza virus genome are transfected, recombinant viruses suitable as vaccines can be recovered by standard purification procedures.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation," and "transduction." A variety of methods can be employed to introduce nucleic acids into cells, including electroporation, calcium phosphate precipitation, lipid mediated transfection (lipofection), and the like.

The term "host cell" means a cell that contains a heterologous nucleic acid, such as a vector or a virus, and supports the replication and/or expression of the nucleic acid. Host cells can be prokaryotic cells such as *E. coli*, or eukaryotic cells such as yeast, insect, amphibian, avian or mammalian cells, including human cells. Non-limiting examples of host cells include Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells), and the like. In certain embodiments, host cells can include eggs (e.g., hen eggs, embryonated hen eggs, and the like). In some cases, 9 to 12-day old embryonated hen eggs are used with the methods herein.

Using the vector system and methods herein, reassortant viruses incorporating six internal gene segments of a strain selected for its desirable properties with respect to vaccine production, and the immunogenic HA and NA segments from a selected, e.g., pathogenic strain such as those provided herein, can be rapidly and efficiently produced in tissue culture and/or eggs. Thus, the system and methods described herein are useful for the rapid production in cell culture and/or eggs of recombinant and reassortant influenza A and B viruses, including viruses suitable for use as vaccines, including live attenuated vaccines, such as, for example, vaccines suitable for intranasal administration.

In such embodiments, typically, a single Master Donor Virus (MDV) strain is selected for each of the A and B subtypes. In certain cases were a live attenuated vaccine is produced, the Master Donor Virus strain is typically chosen for its favorable properties, e.g., temperature sensitivity, cold adaptation and/or attenuation, relative to vaccine production. For example, Master Donor Strains include such temperature sensitive, attenuated and cold adapted strains of A/Ann Arbor/6/60 and B/Ann Arbor/1/66, respectively, as well as others mentioned herein or known in the art.

In some cases, a selected master donor type A virus (MDV-A), or master donor type B virus (MDV-B), can be produced from a plurality of cloned viral cDNAs constituting the viral genome. Embodiments include those where recombinant viruses are produced from eight cloned viral cDNAs. Eight viral cDNAs representing the selected MDV-A or MDV-B sequences of PB2, PB1, PA, NP, HA, NA, M and NS can be cloned into a bi-directional expression vector. The term "vector", as used herein, refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector also can be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In some embodiments, the vectors herein are plasmids. An "expression vector" is a vector, such as a plasmid, that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. As used herein, "expression of a gene" or "expression of a nucleic acid" typically means transcription of DNA into RNA (optionally including modification of the RNA, e.g., splicing) or transcription of DNA into mRNA, translation of RNA into a polypeptide (possibly including subsequent modification of the polypeptide, e.g., post-translational modification), or both transcription and translation, as indicated by the context. A "bi-directional expression vector" is characterized by two alternative promoters oriented in the opposite direction relative to a nucleic acid situated between the two promoters, such that expression can be initiated in both orientations resulting in, for example, transcription of both plus (+) or sense strand, and negative (−) or antisense strand RNAs. Bi-directional expression vectors may be used with the methods provided herein, such as for example pAD3000, such that the viral genomic RNA can be transcribed from an RNA polymerase I (pol I) promoter from one strand and the viral mRNAs can be synthesized from an RNA polymerase II (pol II) promoter from the other strand. Optionally, any gene segment can be modified, including the HA segment, for example, to remove the multi-basic cleavage site (also known as a polybasic cleavage site), in some embodiments.

Following transfection of plasmids bearing the eight viral cDNAs into appropriate host cells, e.g., Vero cells, co-cultured MDCK/293T or MDCK/COS7 cells, infectious recombinant MDV-A or MDV-B virus can be recovered. Using the plasmids and methods described herein and, e.g., in U.S. Pat. No. 8,012,736 and U.S. patent application Ser. No. 12/254,131; Hoffmann, E., 2000, PNAS, 97(11):6108-6113; U.S. Patent Application Publication No. 2002/0164770; and U.S. Pat. No. 6,544,785, the polypeptides provided herein are useful for generating 6:2 reassortant influenza vaccines by co-transfection of the 6 internal genes (PB1, PB2, PA, NP, M and NS) of a selected donor virus (e.g., MDV-A, MDV-B) together with the HA and NA polypeptides derived from different corresponding type (A or B) influenza viruses. For example, the HA segment can be selected from a pathogenically relevant H1, H3 or B strain. Similarly, the HA segment can be selected from a strain with emerging relevance as a pathogenic strain such as those described herein. Reassortants incorporating seven genome segments of the MDV and either the HA or NA gene of a selected strain (7:1 reassortants) can also be produced. It will be appreciated, and as is detailed throughout, molecules provided herein can optionally be combined in any desired combination. For example, the HA and/or NA sequences herein can be placed, for example, into a reassortant backbone such as A/AA/6/60, B/AA/1/66, A/Puerto Rico/8/34 (i.e., PR8), and the like, in 6:2 reassortants or 7:1 reassortants, for example. Thus, as explained in more detail below, there can be 6 internal genome segments from the donor virus and 2 genome segments from a second strain, such as, for example a wild-type or modified strain that is different from the donor strain. Such 2 genome segments are typically the HA and NA genes. For 7:1 reassortants, in which there are 7 genome segments from the donor virus and 1 genome segment (either HA or NA) from a different viral strain, such as, for example a wild-type or modified strain that is different from the donor strain. Often, for 6:2 or 7:1 reassortants, the HA and/or NA is derived from a strain to which an immune response is desired. Also, it will be appreciated that the polypeptide and/or nucleic acid sequences herein can be combined in a number of means in different embodiments herein. Thus, any of the sequences herein can be present singularly in a 7:1 reassortant (i.e., a sequence herein combined with 7 donor virus genome segments) and/or can be present with another sequence provided herein in a 6:2 reassortant. Within such 6:2 reassortants, any of the sequences provided herein can be present with any other sequence herein. Typically, 6:2 reassortants include HA and NA polypeptides from the same strain. For example, certain embodiments can include a 6:2 reassortant having 6 internal genome segments from a donor virus such as, for example A/AA/6/60, and HA and NA genome segments described herein. In some cases, such reassortant viruses include HA and NA genome segments from similar strains.

HA and NA sequences provided herein are optionally utilized in plasmid reassortant vaccines such as those described herein and ts, cs, ca, and/or att viruses and vaccines. The HA and NA sequences provided herein are not limited to specific vaccine compositions or production methods, and can, thus, be utilized in substantially any vaccine type or vaccine production method which utilizes strain specific HA and NA antigens.

FLUMIST®

An example influenza vaccine is FLUMIST (MedImmune Vaccines Inc., Mt. View, Calif.), which is a live, attenuated vaccine that protects children and adults from influenza illness (Belshe et al. (1998) *The efficacy of live attenuated, cold-adapted, trivalent, intranasal influenza virus vaccine in children* N Engl J Med 338:1405-12; Nichol et al. (1999) *Effectiveness of live, attenuated intranasal influenza virus vaccine in healthy, working adults: a randomized controlled trial* JAMA 282:137-44). In certain embodiments, the methods and compositions provided herein can be adapted to/used with production of FLUMIST vaccine. However, the sequences, methods and compositions herein are also adaptable to production of similar or different viral vaccines.

FLUMIST vaccine strains contain, for example, HA and NA gene segments derived from the wild-type strains to which the vaccine is addressed (or, in some instances, to related strains) along with six gene segments, PB1, PB2, PA, NP, M and NS, from a common master donor virus (MDV). The HA and NA sequences herein can thus be included in various FLUMIST formulations. The MDV for influenza A strains of FLUMIST (MDV-A), was created by serial passage of the wild-type A/Ann Arbor/6/60 (A/AA/6/60) strain in primary chicken kidney tissue culture at successively lower temperatures (Maassab (1967) *Adaptation and growth characteristics of influenza virus at 25 degrees C*. Nature 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the is property of MDV-A does not revert following passage through infected hamsters or in shed isolates from children (for a recent review, see Murphy & Coelingh (2002) *Principles underlying the development and use of live attenuated cold-adapted influenza A and B virus vaccines* Viral Immunol 15:295-323).

Methods and Compositions for Prophylactic Administration of Vaccines

In addition to use in production of FLUMIST vaccine, the methods, compositions and polypeptides provided herein can be used in other vaccine formulations. In general, recombinant and reassortant viruses described herein can be administered prophylactically in an immunologically effective amount and in an appropriate carrier or excipient to stimulate an immune response specific for one or more strains of influenza virus as determined by the HA and/or NA sequence.

An "immunologically effective amount" of influenza virus is an amount sufficient to enhance an individual's (e.g., a human's) own immune response against a subsequent exposure to influenza virus. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against influenza virus refers to an immune response exhibited by an individual (e.g., a human) that is protective against disease when the individual is subsequently exposed to and/or infected with wild-type influenza virus. In some instances, the wild-type (e.g., naturally circulating) influenza virus can still cause infection, but it cannot cause a serious or life-threatening infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

Typically, the carrier or excipient for vaccines provided herein is a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected hen eggs (i.e., normal allantoic fluid or NAF), or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, and the like.

Also provided herein are methods for stimulating the immune system of an individual to produce a protective immune response against influenza virus. In such methods, an immunologically effective amount of a recombinant influenza virus provided herein, an immunologically effective amount of a polypeptide provided herein, and/or an immunologically effective amount of a nucleic acid provided herein is administered to the individual in a physiologically acceptable carrier.

Generally, the influenza viruses provided herein are administered in a quantity sufficient to stimulate an immune response specific for one or more strains of influenza virus (i.e., against the HA and/or NA strains provided herein). Typically, administration of the influenza virus elicits a protective immune response to such strains. Dosages and methods for eliciting a protective immune response against one or more influenza strains are known in the art. See, e.g., U.S. Pat. No. 5,922,326; Wright et al., Infect. Immun. 37:397-400 (1982); Kim et al., Pediatrics 52:56-63 (1973); and Wright et al., J. Pediatr. 88:931-936 (1976). For example, influenza viruses are provided in the range of about 1-1000 $HID_{50}$ (human infectious dose), i.e., about $10^5$-$10^8$ pfu (plaque forming units) per dose administered. Typically, the dose will be adjusted within this range based on factors which include age, physical condition, body weight, sex, diet, time of administration, and other clinical factors, for example. The prophylactic vaccine formulation can be systemically administered, e.g., by subcutaneous or intramuscular injection using a needle and syringe, or a needle-less injection device. In some cases, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often used, e.g., an attenuated, cold adapted and/or temperature sensitive recombinant or reassortant influenza virus. While stimulation of a protective immune response with a single dose is typical, additional dosages can be administered, by the same or different route, to achieve the desired prophylactic effect.

Typically, an attenuated recombinant influenza virus provided herein, as used in a vaccine, is sufficiently attenuated such that symptoms of infection, or at least symptoms of serious infection, will not occur in most individuals immunized (or otherwise infected) with the attenuated influenza virus. In some instances, the attenuated influenza virus can still produce symptoms of mild illness (e.g., mild upper respiratory illness) and/or of dissemination to unvaccinated individuals. However, its virulence is sufficiently abrogated such that severe lower respiratory tract infections typically do not occur in the vaccinated or incidental host.

In some cases, an immune response can be stimulated by ex vivo or in vivo targeting of dendritic cells with influenza viruses containing the sequences provided herein. For example, proliferating dendritic cells can be exposed to viruses in a sufficient amount and for a sufficient period of time to permit capture of the influenza antigens by dendritic cells. The cells are then transferred into a subject to be vaccinated by standard intravenous transplantation methods.

While stimulation of a protective immune response with a single dose is typical, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Optionally, the formulation for prophylactic administration of the influenza viruses also contains one or more adjuvants for enhancing the immune response to the influenza antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59.

In some cases, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, and the like. The immunostimulatory molecules can be administered in the same formulation as the influenza viruses, or can be administered separately. Either the protein (e.g., an HA and/or NA polypeptide provided herein) or an expression vector encoding the protein can be administered to produce an immunostimulatory effect.

The above described methods can be useful for therapeutically and/or prophylactically treating a disease or disorder, typically influenza, by introducing a vector comprising a heterologous polynucleotide encoding a therapeutically or prophylactically effective HA and/or NA polypeptide (or peptide) or HA and/or NA RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences, e.g., as described herein. Optionally, more than one heterologous coding sequence is incorporated into a single vector or virus. For example, in addition to a polynucleotide encoding a therapeutically or prophylactically active HA and/or NA polypeptide or RNA, the vector can also include additional therapeutic or prophylactic polypeptides, e.g., antigens, co-stimulatory molecules, cytokines, antibodies, and/or markers, and the like.

Although vaccination of an individual with an attenuated influenza virus of a particular strain of a particular subgroup can induce cross-protection against influenza viruses of different strains and/or subgroups, cross-protection can be enhanced, if desired, by vaccinating the individual with attenuated influenza virus from at least two (i.e. bivalent), at least three (i.e. trivalent), or at least four (i.e. tetravalent) influenza virus strains or substrains, e.g., at least two of which may represent a different subgroup. For example, vaccinating an individual with at least four strains or substrains of attenuated influenza virus (i.e. tetravalent vaccine) may include vaccinating the individual with at least two strains or substrains of influenza A virus and at least two strains or substrains of influenza B virus. Vaccinating an individual with the at least four strains or substrains of attenuated influenza virus (i.e. tetravalent) may include vaccinating the individual with at least three strains or substrains of influenza A virus and at least one strain or substrain of influenza B virus. The vaccination of the individual with at least four influenza virus strains or substrains may require administration of a single tetravalent vaccine which comprises all of the at least four attenuated influenza virus strains or substrains. In some cases, the vaccination may require administration of multiple vaccines, each of which includes one, two, or three of the attenuated influenza virus strains or substrains. Additionally, vaccine combinations can optionally include mixes of pandemic vaccines and non-pandemic strains. Vaccine mixtures (or multiple vaccinations) can include components from human strains and/or non-human influenza strains (e.g., avian and human). Similarly, the attenuated influenza virus vaccines provided herein can optionally be combined with vaccines that induce protective immune responses against other infectious agents. In some embodiments, a vaccine provided herein is a trivalent vaccine comprising three reassortant influenza viruses. In some embodiments, a vaccine provided herein is a trivalent vaccine comprising two reassortant influenza A viruses and a reassortant influenza B virus. In some embodiments, a vaccine provided herein is a trivalent vaccine comprising a reassortant influenza A virus of the H1 type, a reassortant influenza A virus of the H3 type and a reassortant influenza B virus. In some embodiments, a vaccine provided herein is a tetravalent vaccine comprising four reassortant influenza viruses. In some embodiments, a vaccine provided herein is a tetravalent vaccine comprising two reassortant influenza A viruses and two reassortant influenza B viruses.

In some embodiments, a vaccine provided herein is a tetravalent vaccine comprising a reassortant influenza A virus of the H1 type, a reassortant influenza A virus of the H3 type, a reassortant influenza B virus of the Victoria lineage and a reasortant influenza B virus of the Yamagata lineage. In some cases, a tetravalent vaccine can include one or more influenza viruses having one or more modified HA polypeptides described herein. For example, for a tetravalent vaccine having at least one influenza A virus, such as an influenza A virus of the H1 type mentioned above, the HA polypeptide can include any of the amino acid substitutions described herein, including, for example, D127E, N125D/D127E, or N125E/D127E, where the modifications are at positions corresponding to positions in SED ID NO:1. In some cases, a tetravalent vaccine includes all or parts of the Gilroy11 virus, such as the HA polypeptide with any modifications described herein.

Production of Recombinant Virus

Negative strand RNA viruses can be genetically engineered and recovered using a recombinant reverse genetics approach (U.S. Pat. No. 5,166,057). Such a method was originally applied to engineer influenza viral genomes (Luytjes et al. (1989) Cell 59:1107-1113; Enami et al. (1990) Proc. Natl. Acad. Sci. USA 92:11563-11567), and has been successfully applied to a wide variety of segmented and nonsegmented negative strand RNA viruses, e.g., rabies (Schnell et al. (1994) EMBO J. 13: 4195-4203); VSV (Lawson et al. (1995) Proc. Natl. Acad. Sci. USA 92: 4477-4481); measles virus (Radecke et al. (1995) EMBO J. 14:5773-5784); rinderpest virus (Baron & Barrett (1997) J. Virol. 71: 1265-1271); human parainfluenza virus (Hoffman & Banerjee (1997) J. Virol. 71: 3272-3277; Dubin et al. (1997) Virology 235:323-332); SV5 (He et al. (1997) Virology 237:249-260); canine distemper virus (Gassen et al. (2000) J. Virol. 74:10737-44); and Sendai virus (Park et al. (1991) Proc. Natl. Acad. Sci. USA 88: 5537-5541; Kato et al. (1996) Genes to Cells 1:569-579). Recombinant influenza viruses produced according to such methods are contemplated herein, as are recombinant influenza virus comprising one or more nucleic acids and/or polypeptides provided herein. Influenza viruses in general (and those provided herein) are negative stranded RNA viruses. Thus, when influenza viruses are described herein as comprising one or more sequences provided herein, it is to be understood that the corresponding negative stranded RNA version of each sequence are referred to as well. The nucleotide sequences provided herein typically comprise DNA versions (e.g., coding plus sense) of the genes (along with some untranslated regions in the nucleotide sequences, in some cases). Conversions between RNA and DNA sequences can be performed, for example, by changing U to T or T to U. Other sequence conversions, e.g., from a nucleotide sequence to the corresponding amino acid sequence or to a corresponding complementary sequence (whether DNA or RNA), also can be performed using methods known in the art. Also, when such HA and/or NA sequences are described within DNA vectors, e.g., plasmids, the corresponding DNA version of the sequences are typically to be understood. Nucleic acids provided herein thus include the explicit sequences in the sequence listings herein, as well as the complements of such sequences (both RNA and DNA), the double stranded form of the sequences provided herein, the corresponding RNA forms of the sequences provided herein (either as the RNA complement to the explicit sequence provided herein or as the RNA version of the sequence provided herein, e.g., of the same sense, but comprised of RNA, with U in place of T.

Cell Culture and Expression Hosts

In some embodiments, the polypeptides provided herein are produced by recombinant techniques. In some cases, host cells are genetically engineered (i.e., transduced, transformed or transfected) with a vector, such as an expression vector. As described above, the vector can be in the form of a plasmid, a viral particle, a phage, and the like. Non-limiting examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; and insect cells such as *Drosophila* and *Spodoptera frugiperda.*

In some cases, mammalian cells are used to culture the HA and NA molecules provided herein. Suitable host cells for the replication of influenza virus (e.g., with the HA and/or NA sequences herein) include, e.g., Vero cells, BHK cells, MDCK cells, 293 cells and COS cells, including 293T cells, COS7 cells or the like. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, and the like, and/or additional nutrients, such as L-glutamine, sodium pyruvate, non-essential amino acids, additional supplements to promote favorable growth characteristics, e.g., trypsin, β-mercaptoethanol, and the like.

The engineered host cells can be cultured in conventional nutrient media modified as appropriate for activating promoters, selecting transformants, or amplifying the inserted polynucleotide sequences, e.g., through production of viruses. The culture conditions, such as temperature, pH and the like, are those typically used with the particular host cell selected for expression, and are generally known in the art. Additionally, variations in such procedures adapted to the compositions and methods herein can be readily determined through routine experimentation.

Cells for production of influenza virus (e.g., having the HA and/or NA sequences provided herein) can be cultured in serum-containing or serum-free medium. In some cases, e.g., for the preparation of purified viruses, it is typically desirable to grow the host cells in serum-free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., CYTO3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume it is often important that the cultures be maintained at an appropriate temperature, to insure efficient recovery of recombinant and/or reassortant influenza virus using temperature dependent multi plasmid systems (see, e.g., U.S. Pat. No. 8,012,736 and U.S. patent application Ser. No. 12/254,131), heating of virus solutions for filtration, and the like. Typically, a regulator, e.g., a thermostat, or other device for sensing and maintaining the temperature of the cell culture system and/or other solution, is employed to insure that the temperature is at the correct level during the appropriate period (e.g., virus replication).

In some embodiments, where reassorted viruses are to be produced from segments on vectors, for example, vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TRANSIT-LT1 (Mirus) according to the manufacturer's instructions to produce reassorted viruses. In certain cases, for example, approximately 1 microgram of each vector is introduced into a population of host cells with approximately 2 microliters of TRANSIT-LT1 diluted in 160 µl medium, e.g., serum-free medium, in a total volume of 200 microliters. The DNA:transfection reagent mixtures are incubated at room temperature for 45 minutes followed by addition of 800 microliters of medium. The transfection mixture is added to the host cells, and the cells are cultured as described or with other methods known in the art. Accordingly, for the production of recombinant or reassortant viruses in cell culture, vectors incorporating each of the 8 genome segments, (PB2, PB1, PA, NP, M, NS, HA and NA) are mixed with approximately 20 microliters TRANSIT-LT1 and transfected into host cells. Optionally, serum-containing medium is replaced prior to transfection with serum-free medium, e.g., OPTI-MEM I, and incubated for 4-6 hours.

Electroporation also can be employed to introduce such vectors incorporating influenza genome segments into host cells. For example, plasmid vectors incorporating an influenza A or influenza B virus are favorably introduced into Vero cells using electroporation according to the following procedure. In brief, approximately $5 \times 10^6$ Vero cells, e.g., grown in Modified Eagle's Medium (MEM) supplemented with 10% Fetal Bovine Serum (FBS) are resuspended in 0.4 ml OPTI-MEM and placed in an electroporation cuvette. Twenty micrograms of DNA in a volume of up to 25 microliters is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

In mammalian host cells, a number of expression systems, such as viral-based systems, can be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing the polypeptides of interest in infected host cells (Logan and Shenk (1984) Proc Natl Acad Sci 81:3655-3659). In addition, transcription enhancers, such as the rous sarcoma virus (RSV) enhancer, can be used to increase expression in mammalian host cells.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing, which cleaves a precursor form into a mature form, of the protein is sometimes important for correct insertion, folding and/or function. Additionally proper location within a host cell (e.g., on the cell surface) is also important. Different host cells such as COS, CHO, BHK, MDCK, 293, 293T, COS7, and the like, have specific cellular machinery and characteristic mechanisms for such post-translational activities and can be chosen to ensure the correct modification and processing of the current introduced, foreign protein.

For long-term, high-yield production of recombinant proteins encoded by, or having subsequences encoded by, the polynucleotides provided herein, stable expression systems are optionally used. For example, cell lines, stably expressing a polypeptide provided herein, are transfected using expression vectors that contain viral origins of replication or endogenous expression elements and a selectable marker gene. For example, following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Thus, resistant clumps of stably transformed cells, e.g., derived from single cell type, can be proliferated using tissue culture techniques appropriate to the cell type.

Host cells transformed with a nucleotide sequence encoding a polypeptide provided herein are optionally cultured under conditions suitable for the expression and recovery of the encoded protein from cell culture. The cells expressing said protein can be sorted, isolated and/or purified. The protein or fragment thereof produced by a recombinant cell can be secreted, membrane-bound, or retained intracellularly, depending on the sequence (e.g., depending upon fusion proteins encoding a membrane retention signal or the like) and/or the vector used.

Expression products corresponding to the nucleic acids provided herein also can be produced in non-animal cells such as plants, yeast, fungi, bacteria and the like. In bacterial systems, a number of expression vectors can be selected depending upon the use intended for the expressed product. For example, when large quantities of a polypeptide or fragments thereof are needed for the production of antibodies, vectors that direct high-level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., sequences comprising those found herein, can be ligated into the vector in-frame with sequences for the amino-terminal translation initiating methionine and the subsequent 7 residues of beta-galactosidase producing a catalytically active beta galactosidase fusion protein; pIN vectors (Van Heeke & Schuster (1989) J Biol Chem 264:5503-5509); pET vectors (Novagen, Madison Wis.); and the like. Similarly, in the yeast *Saccha-*

*romyces cerevisiae* a number of vectors containing constitutive or inducible promoters such as alpha factor, alcohol oxidase and PGH can be used for production of the desired expression products. For reviews, see Ausubel, infra, and Grant et al., (1987); Methods in Enzymology 153:516-544.

Isolation, Cloning, Mutagenesis and Expression of Biomolecules of Interest

Various types of cloning and mutagenesis methods can be used with the methods herein, e.g., to produce and/or isolate, e.g., novel or newly isolated HA and/or NA molecules and/or to further modify/mutate the polypeptides (e.g., HA and NA molecules) provided herein. As used herein, the term "isolated" refers to a biological material, such as a virus, a nucleic acid or a protein, which is substantially free from components that normally accompany or interact with it in its naturally occurring environment. The isolated biological material optionally comprises additional material not found with the biological material in its natural environment, e.g., a cell or wild-type virus. For example, if the material is in its natural environment, such as a cell, the material can have been placed at a location in the cell (e.g., genome or genetic element) not native to such material found in that environment. For example, a naturally occurring nucleic acid (e.g., a coding sequence, a promoter, an enhancer, and the like) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

In some embodiments, isolated nucleic acids, polypeptides and/or viruses can be further mutated. Mutagenesis methods include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA and the like. Additional suitable mutagenesis methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the methods herein. In some embodiments, mutagenesis can be guided by known information of the naturally occurring molecule or altered or mutated naturally occurring molecule, e.g., sequence, sequence comparisons, physical properties, crystal structure or the like.

Oligonucleotides for use in mutagenesis (e.g., mutating libraries of the HA and/or NA molecules provided herein, or altering such) are typically synthesized chemically according to the solid phase phosphoramidite triester method described by Beaucage and Caruthers, Tetrahedron Letts 22(20):1859-1862, (1981) using an automated synthesizer, as described in Needham-VanDevanter et al., Nucleic Acids Res, 12:6159-6168 (1984). In addition, essentially any nucleic acid can be custom or standard ordered from any of a variety of commercial sources Similarly, peptides and antibodies can be custom ordered from any of a variety of sources.

Also provided herein are host cells and organisms comprising a HA and/or NA molecule or other polypeptide and/or nucleic acid provided herein or such HA and/or NA or other sequences within various vectors such as 6:2 reassortant influenza viruses, plasmids in plasmid rescue systems, and the like. Host cells can be genetically engineered (e.g., transformed, transduced or transfected) with the vectors provided herein, which can be, for example, a cloning vector or an expression vector. The vector can be, for example, in the form of a plasmid, a bacterium, a virus, a naked polynucleotide, or a conjugated polynucleotide. The vectors can be introduced into cells and/or microorganisms by standard methods including electroporation (see, From et al., Proc Natl Acad Sci USA 82, 5824 (1985), infection by viral vectors, high velocity ballistic penetration by small particles with the nucleic acid either within the matrix of small beads or particles, or on the surface (Klein et al., Nature 327, 70-73 (1987)).

Several well-known methods of introducing target nucleic acids into bacterial cells are available, any of which can be used with the methods herein. These include, for example, fusion of the recipient cells with bacterial protoplasts containing the DNA, electroporation, projectile bombardment, and infection with viral vectors, and the like. Bacterial cells can be used to amplify the number of plasmids containing DNA constructs. The bacteria are grown to log phase and the plasmids within the bacteria can be isolated by a variety of methods known in the art. In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith, Gene 8:81 (1979); Roberts, et al., Nature, 328:731 (1987); Schneider, B., et al., Protein Expr Purif 6435:10 (1995); Ausubel, Sambrook, Berger (all supra). A catalogue of Bacteria and Bacteriophages useful for cloning is provided, e.g., by the ATCC, e.g., The ATCC Catalogue of Bacteria and Bacteriophage (1992) Gherna et al. (eds.) published by the ATCC. Additional basic procedures for sequencing, cloning and other aspects of molecular biology and underlying theoretical considerations are known in the art.

Polypeptide Production and Recovery

In some embodiments, following transduction of a suitable host cell line or strain and growth of the host cells to an appropriate cell density, a selected promoter is induced by appropriate means (e.g., temperature shift or chemical induction) and cells are cultured for an additional period. In some embodiments, a secreted polypeptide product, e.g., a HA and/or NA polypeptide as in a secreted fusion protein form, is then recovered from the culture medium. In some embodiments, a virus particle containing one or more HA and/or NA polypeptides provided herein is produced from the cell. In some cases, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are known in the art. Additionally, cells expressing a HA and/or a NA polypeptide provided herein can be utilized without separating the polypeptide from the cell. In such situations, the polypeptide is optionally expressed on the cell surface and is examined thus (e.g., by having HA and/or NA molecules, or fragments thereof, e.g., comprising fusion proteins or the like) on the cell surface bind antibodies, for example. Such cells are also provided herein.

Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems known in the art), hydroxylapatite chromatography, and lectin chromatography. Protein refolding steps can be used, as desired, in completing configuration of the mature protein. Also, high performance liquid chromatography (HPLC) can be employed in the final purification steps.

When the expressed polypeptides, such as the polypeptides provided herein, are produced in viruses, the viruses are typically recovered from the culture medium, in which infected (transfected) cells have been grown. Typically, crude medium is clarified prior to concentration of influenza viruses. Common methods include ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. In some cases, and for most large-scale commercial applications, virus is elutriated from density gradients using a zonal-centrifuge rotor operating in continuous mode. Additional details regarding the preparation of influenza viruses from tissue culture are provided, e.g., in U.S. Pat. No. 5,690,937. If desired, the recovered viruses can be stored at −80° C. in the presence of sucrose-phosphate-glutamate (SPG) as a stabilizer.

Modified Amino Acids

Expressed polypeptides, such as the polypeptides provided herein, can contain one or more modified amino acids. The presence of modified amino acids can be advantageous in, for example, (a) increasing polypeptide serum half-life, (b) reducing/increasing polypeptide antigenicity, and/or (c) increasing polypeptide storage stability. Amino acid(s) can be modified, for example, co-translationally or post-translationally during recombinant production (e.g., N-linked glycosylation at N—X—S/T motifs during expression in mammalian cells) or modified by synthetic means (e.g., via PEGylation).

Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like, as well as amino acids modified by conjugation to, e.g., lipid moieties or other organic derivatizing agents.

Fusion Proteins

Also provided herein are fusion proteins comprising fusions of the sequences provided herein (e.g., encoding HA and/or NA polypeptides) or fragments thereof with, e.g., immunoglobulins (or portions thereof), sequences encoding, e.g., GFP (green fluorescent protein), or other similar markers. Nucleotide sequences encoding such fusion proteins are also provided herein. Fusion proteins can be used for, e.g., similar applications (including, e.g., therapeutic, prophylactic, diagnostic, experimental, and the like applications as described herein) as the non-fusion proteins provided herein. In addition to fusion with immunoglobulin sequences and marker sequences, the proteins provided herein also can be fused with, e.g., sequences which allow sorting of the fusion proteins and/or targeting of the fusion proteins to specific cell types, regions, and the like.

Antibodies

The polypeptides provided herein can be used to produce antibodies specific for the polypeptides provided herein and/or polypeptides encoded by the polynucleotides provided herein, and conservative variants thereof. Antibodies specific for the above mentioned polypeptides are useful, e.g., for diagnostic and therapeutic purposes, e.g., related to the activity, distribution, and expression of target polypeptides. For example, such antibodies can optionally be utilized to define other viruses within the same strain(s) as the HA/NA sequences herein.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the $(Fab')_2$ dimer into a Fab' monomer. The Fab' monomer is essentially a Fab with part of the hinge region (see Fundamental Immunology, W. E. Paul, ed., Raven Press, N.Y. (1999) for a more detailed description of other antibody fragments). While various antibody fragments are defined in terms of the digestion of an intact antibody, such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include, e.g., polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Antibodies specific for the polypeptides provided herein can be generated by methods well known in the art. Such antibodies can include, but are not limited to, polyclonal, monoclonal, chimeric, humanized, single chain, Fab fragments and fragments produced by an Fab expression library.

Polypeptides often do not require biological activity for antibody production (e.g., full length functional hemagglutinin or neuraminidase is often not required). However, the polypeptide or oligopeptide is typically antigenic. Peptides used to induce specific antibodies typically have an amino acid sequence of at least about 4 amino acids, and often at least 5 or 10 amino acids. Short stretches of a polypeptide can be fused with another protein, such as keyhole limpet hemocyanin, and an antibody is produced against the chimeric molecule.

Numerous methods for producing polyclonal and monoclonal antibodies are known in the art. Some suitable techniques for antibody preparation include selection of libraries of recombinant antibodies in phage or similar vectors. See, Huse et al. (1989) Science 246: 1275-1281; and Ward, et al. (1989) Nature 341: 544-546. Specific monoclonal and polyclonal antibodies and antisera will usually bind with a $K_D$ of, e.g., at least about 0.1 micromolar, at least about 0.01 micromolar or better, and, typically and at least about 0.001 micromolar or better. For certain therapeutic applications, humanized antibodies are desirable. Detailed methods for preparation of chimeric (humanized) antibodies can be found in U.S. Pat. No. 5,482,856.

Nucleic Acid and Polypeptide Sequence Variants

Provided herein are modified viral polynucleotides and polypeptides, e.g., hemagglutinin and neuraminidase sequences, and, e.g., compositions and methods comprising such polynucleotides and polypeptides. Examples of sequences are disclosed herein. However, polypeptides and/or polynucleotides that can be used are not necessarily limited to those sequences disclosed herein and that related and unrelated sequences with the functions described herein, e.g., encoding a HA and/or a NA molecule, also can be made and used.

Provided herein are variants of the disclosed sequences. For example, conservative variations of the disclosed sequences that yield a functionally identical sequence are included herein. Variants of the polynucleotide sequences, where the variants hybridize to at least one disclosed sequence or complement thereof, also are included herein. In some cases, a variant can hybridize to a disclosed sequence under certain hybridization conditions or stringency levels, such as, for example, medium or high stringency. Unique subsequences of the disclosed sequences, as determined by, e.g., standard sequence comparison techniques, also are included herein.

Also provided herein are polypeptide variants. The term "variant" with respect to a polypeptide refers to an amino acid sequence that is altered by one or more amino acids with respect to a reference sequence. In some cases, the reference sequence is a "wild-type", "native" or "unmodified" polypeptide sequence. The variant can have "conservative" changes, where a substituted amino acid has similar structural or chemical properties, e.g., replacement of leucine with isoleucine. In some cases, a variant can have "non-conservative" changes, e.g., replacement of a glycine with a tryptophan. Analogous minor variations also can include amino acid deletion or insertion, or both. In some cases, a variant can have 1 to 10 amino acid modifications, e.g., substitutions (e.g., conservative or non-conservative), additions or deletions, or a combination of these. In some cases, the modified amino acids are non-consecutive amino acids. In some cases, a variant has 90%-99% identity to a sequence provided herein, such as, for example SEQ ID NOs:1, 2, 5, 7, but retain certain amino acids or codons at specific positions necessary to retain HA function and/or viral replication in eggs. Guidance in determining which amino acid residues can be substituted, inserted, or deleted without eliminating biological or immunological activity can be found using computer programs well known in the art, for example, DNASTAR software. Examples of conservative substitutions are also described herein.

Other polypeptide variants herein include, for example, polypeptides with one or more amino acid substitutions. In some embodiments, one or more amino acid substitutions are made in an HA and/or NA polypeptide. HA polypeptide amino acid substitutions are described in further detail below.

HA Amino Acid Substitutions

Provided herein are modified hemagglutinin (HA) polypeptides that have one or more amino acid substitutions. Typically, an amino acid substitution is a replacement of a native amino acid (i.e. native residue) at a particular position in an amino acid sequence with an non-native amino acid (i.e. non-native residue). The native and modified HA polypeptides described herein can be any influenza HA polypeptide. In some cases, the HA polypeptide is a swine influenza virus hemagglutinin. In some cases, the HA polypeptide is an H1 virus hemagglutinin. In some cases, the HA polypeptide is an A/Gilroy/231/2011 (Gilroy 11) virus hemagglutinin, having a native amino acid sequence of, for example, SEQ ID NO:1 or SEQ ID NO:28. In some cases, the HA polypeptide is an A/California/7/2009 virus hemagglutinin, having a native amino acid sequence of, for example, SEQ ID NO:7 or SEQ ID NO:30. In some cases, the HA polypeptide is a mature HA polypeptide, having a native amino acid sequence of SEQ ID NO:1 or SEQ ID NO:7. In some cases, the HA polypeptide includes the HA1 peptide. In some cases, the HA polypeptide comprises a fragment, such as, for example, a fragment of SEQ ID NO:1 or SEQ ID NO:7. In some cases, the HA polypeptide comprises a fragment which includes residues 125 and 127 of SEQ ID NO:1 or residues corresponding to positions 125 and 127 of SEQ ID NO:1. In some cases, the fragment may not include certain N-terminal and/or certain C-terminal amino acids of the HA polypeptide. For example, a fragment may not include some or all of the first 100 N-terminal amino acids and/or may not include some or all of the last 100 C-terminal amino acids. In some cases, the fragment comprises about 200 or more contiguous amino acids of an HA polypeptide. For example, an HA polypeptide fragment may comprise about 220, 240, 260, 280, 300, 320, 330, 340, 360, 380, 400, 420, 460, 480, 500 or more contiguous amino acids. In some cases, the HA polypeptide includes amino acids 1-320, 1-321, 1-322, 1-323, 1-324, 1-325, 1-326, 1-327, 1-328, 1-329, or 1-330 of SEQ ID NO:1 or SEQ ID NO:7. In some cases, the HA polypeptide includes amino acids 1-327 of SEQ ID NO:1 or SEQ ID NO:7.

In some embodiments, the hemagglutinin polypeptide includes an amino acid substitution at position 125 (of a mature HA polypeptide), or at a position corresponding to residue 125 of SEQ ID NO:1. As used herein, "a position corresponding to" means an equivalent amino acid position in any HA amino acid sequence when aligned with the sequence of SEQ ID NO:1. It is understood that reference to amino acid positions herein include such equivalent amino acid positions in other HA polypeptides. Methods for sequence alignment are described in further detail below. In some embodiments, the hemagglutinin polypeptide includes a substitution at position 127 (of a mature HA polypeptide), or at a position corresponding to residue 127 of SEQ ID NO:1. In some embodiments, the native amino acid at position 125 and/or 127 is substituted with an acidic residue. Acidic amino acids are amino acids with acidic side chains having a second carboxyl group and are polar and negatively charged at physiological pH. Acidic amino acids include glutamic acid (E) and aspartic acid (D). In some cases, the native amino acid at position 125 is substituted with an aspartic acid (D). In some cases, the native amino acid at position 125 is substituted with a glutamic acid (E). In some cases, the native amino acid at position 127 is substituted with a glutamic acid (E). In some cases, the native amino acid at position 125 is substituted with an aspartic acid (D) and the native amino acid at position 127 is substituted with a glutamic acid (E). In some cases, the native amino acid at position 125 is substituted with a glutamic acid (E) and the native amino acid at position 127 is substituted with a glutamic acid (E). Also provided are polynucleotides encoding any of the foregoing polypeptides and complements thereof.

In some embodiments, one or more amino acids are substituted in an A/Gilroy/231/2011 (Gilroy 11) virus hemagglutinin having the native amino acid sequence of SEQ ID NO:1. In some cases, the asparagine (N) at position 125 of SEQ ID NO:1 is substituted with an aspartic acid (D). In some cases, the asparagine (N) at position 125 of SEQ ID NO:1 is substituted with a glutamic acid (E). In some cases, the aspartic acid (D) at position 127 of SEQ ID NO:1 is substituted with a glutamic acid (E). In some cases, the asparagine (N) at position 125 of SEQ ID NO:1 is substituted with an aspartic acid (D), and the aspartic acid (D) at position 127 of SEQ ID NO:1 is substituted with a glutamic acid (E). In some cases, the asparagine (N) at position 125 of SEQ ID NO:1 is substituted with a glutamic acid (E) and the aspartic acid (D) at position 127 of SEQ ID NO:1 is substituted with a glutamic acid (E). Also provided are polynucleotides encoding any of the foregoing polypeptides and complements thereof.

In some embodiments, one or more amino acids are substituted in an A/California/7/2009 virus hemagglutinin having the native amino acid sequence of SEQ ID NO:7. In some cases, the asparagine (N) at position 125 of SEQ ID NO:7 is substituted with an aspartic acid (D). In some cases, the asparagine (N) at position 125 of SEQ ID NO:7 is substituted with a glutamic acid (E). In some cases, the aspartic acid (D) at position 127 of SEQ ID NO:7 is substituted with a glutamic acid (E). In some cases, the asparagine (N) at position 125 of SEQ ID NO:7 is substituted with an aspartic acid (D), and the aspartic acid (D) at position 127 of SEQ ID NO:7 is substituted with a glutamic acid (E). In some cases, the asparagine (N) at position 125 of SEQ ID NO:7 is substituted with a glutamic acid (E) and the aspartic acid (D) at position 127 of SEQ ID NO:7 is substituted with a glutamic acid (E). Also provided are polynucleotides encoding any of the foregoing polypeptides and complements thereof.

Increasing Peak Titer in Eggs

In some embodiments, the HA modifications are substitutions that can increase peak titer in embryonated eggs for a reassortant or recombinant influenza virus having a modified HA polypeptide described herein. The peak titer can be increased between about 1.5-fold to about 40-fold, for example 2-fold, 4-fold, 8-fold, 10-fold, 20-fold or 30-fold relative to the same reassortant or recombinant influenza having an unmodified HA polypeptide.

In some cases, peak titer can be further increased for reassortants having a native or modified neuraminidase (NA) polypeptide from the same or a different viral strain as the HA polypeptide. In some cases, the NA polypeptide is a swine influenza virus NA. In some cases, the neuraminidase is an N1 neuraminidase. In some embodiments, the reassortant or recombinant viruses described herein include a NA polypeptide from a viral strain that typically grows well in embryonated eggs. For example, the reassortants herein can include an NA from the A/Brisbane/10/10 virus comprising an amino acid sequence of SEQ ID NO:6, or a fragment thereof.

The modified HA polypeptides described herein can include additional amino acid substitutions. In some embodiments, the additional amino acid substitutions are substitutions that can further increase peak titer in embryonated eggs for a reassortant or recombinant influenza virus having a modified HA polypeptide. Non-limiting examples of additional amino acid substitutions include K119E, A186D, D222G, N97D, K205R, V216I, L249V, and E283K, or equivalents, where position numbers and native residues are according to the amino acid sequence of SEQ ID NO:1.

Silent Variations

Due to the degeneracy of the genetic code, any of a variety of nucleic acid sequences encoding polypeptides and/or viruses provided herein are optionally produced, some which can bear lower levels of sequence identity to the HA and NA nucleic acid and polypeptide sequences herein. The following provides a typical codon table specifying the genetic code, found in many biology and biochemistry texts.

TABLE 1

Codon table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The codon table shows that many amino acids are encoded by more than one codon. For example, the codons AGA, AGG, CGA, CGC, CGG, and CGU all encode the amino acid arginine. Thus, at every position in a nucleic acid where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations," discussed below. Each codon in a nucleic acid (except ATG, which is ordinarily the only codon for methionine, and TTG, which is ordinarily the only codon for tryptophan) can be modified by standard techniques to encode a functionally identical polypeptide. Accordingly, each silent variation of a nucleic acid which encodes a polypeptide is implicit in any described sequence. The sequences provided herein, therefore, explicitly provide each and every possible variation of a nucleic acid sequence encoding a polypeptide provided herein that could be made by selecting combinations based on possible codon choices. These combinations are made in accordance with the standard triplet genetic code (e.g., as set forth in Table 1, or as is commonly available in the art) as applied to the nucleic acid sequence encoding a hemagglutinin or a neuraminidase polypeptide herein. All such variations of every nucleic acid herein are specifically provided and described by consideration of the sequence in combination with the genetic code. Such silent substitutions can be made using the methods herein.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence provided herein which encodes an amino acid. Similarly, "conservative amino acid substitutions," in one or a few amino acids in an amino acid sequence are substituted with different amino acids with highly similar properties, are also readily identified as being highly similar to a disclosed construct such as those herein. Such conservative variations of each disclosed sequence are included herein.

"Conservative variation" of a particular nucleic acid sequence refers to those nucleic acids which encode identical or essentially identical amino acid sequences, or, where the nucleic acid does not encode an amino acid sequence, to essentially identical sequences, see, Table 2 below. Individual substitutions, deletions or additions which alter, add or delete a single amino acid or a small percentage of amino acids (typically less than 5%, more typically less than 4%, 3%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence herein include substitutions of a small percentage, typically less than 5%, more typically less than 4%, 3%, 2% or 1%, of the amino acids of the polypeptide sequence, with a conservatively selected amino acid of the same conservative substitution group. The addition of sequences which do not alter the encoded activity of a nucleic acid molecule, such as the addition of a non-functional sequence, is a conservative variation of the basic nucleic acid.

TABLE 2

| Conservative substitution groups | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Sequence Comparison, Identity and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms known in the art) or by visual inspection.

The phrase "substantially identical," in the context of two nucleic acids or polypeptides (e.g., DNAs and/or RNAs encoding a HA or NA molecule, or the amino acid sequence of a HA or NA molecule) refers to two or more sequences or subsequences that have at least about 90%, 91%, 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. In some cases, "substantial identity" exists over a region of the amino acid sequences that is at least about 200 residues in length or over a region of at least about 250 residues, or the sequences are substantially identical over at least about 300 residues, 350 residues, 400 residues, 425 residues, 450 residues, 475 residues, 480 residues, 490 residues, 495 residues, 499 residues, 500 residues, 502 residues, 559 residues, 565 residues, or 566 residues, or over the full length of the two sequences to be compared when the amino acids are hemagglutinin or hemagglutinin fragments or which is substantially identical over at least about 350 amino acids; over at least about 400 amino acids; over at least about over at least about 436 amino acids, over at least about 450 amino acids; over at least about 451 amino acids; over at least about 465 amino acids; over at least about 466 amino acids; over at least about 469 amino acids; over at least about 470 amino acids; or over at least about 566 amino acids contiguous when the amino acid is neuraminidase or a neuraminidase fragment.

For nucleotide sequences, substantially identical sequences can include substantially complementary sequences. As used to herein, "substantially complementary" with respect to sequences refers to nucleotide sequences that will hybridize with each other under certain hybridization conditions or stringency levels, such as, for example medium or high stringency. As used herein, the term "stringency" refers to conditions for hybridization and washing. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60°

C. In some cases, stringent hybridization conditions are hybridization in 6× sodium chloride/sodium citrate (SSC) at about 45° C., followed by one or more washes in 0.2×SSC, 0.1% SDS at 65° C. In some cases, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents such as formamide, for example. Organic solvents, like formamide, reduce the thermal stability of double-stranded polynucleotides, so that hybridization can be performed at lower temperatures, while still maintaining stringent conditions.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv Appl Math 2:482 (1981), by the homology alignment algorithm of Needleman & Wunsch, J Mol Biol 48:443 (1970), by the search for similarity method of Pearson & Lipman, Proc Natl Acad Sci USA 85:2444 (1988), by computerized implementations of algorithms such as GAP, BESTFIT, FASTA, and TFASTA in the Wisconsin Genetics Software Package, Genetics Computer Group, 575 Science Dr., Madison, Wis., or by visual inspection.

One example of an algorithm that is suitable for determining percent sequence identity and sequence similarity is the BLAST algorithm, which is described in Altschul et al., J Mol Biol 215:403-410 (1990). Software for performing BLAST analyses is publicly available through the National Center for Biotechnology Information (world wide web URL address: ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (see, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) Proc Natl Acad Sci USA 89:10915).

In addition to calculating percent sequence identity, the BLAST algorithm also performs a statistical analysis of the similarity between two sequences (see, e.g., Karlin & Altschul, Proc Natl Acad Sci USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) CABIOS 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple nucleic acid, or amino acid, sequence alignments is the CLUSTALW program (Thompson, J. D. et al. (1994) Nucl. Acids. Res. 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) Proc. Natl. Acad. Sci. USA 89: 10915-10919.

EXAMPLES

The examples set forth below illustrate certain embodiments and do not limit the technology.

Example 1

Materials and Methods

The materials and methods set forth in this Example were used to perform the experiments described in subsequent examples.

cDNA Cloning of HA and NA Segments of A/Gilroy/231/2011

The following is a description of the method for cDNA cloning of HA and NA segments of A/Gilroy/231/2011 (Gilroy11).

Viral RNA Extraction

An H1N1 virus, A/Gilroy/231/2011 (Gilroy11), was isolated from ferret nasal wash samples. For viral RNA extraction, a QIAAMP viral RNA mini kit (Qiagen catalog #52904) was used to extract viral RNA from 140 microliters of the wild-type A/Gilroy/231/2011 (Gilroy11) virus. The RNA was eluted in 60 microliters of AVE buffer.

RT-PCR

For reverse transcriptase polymerase chain reaction (RT-PCR), SUPERSCRIPT III one-step RT-PCR system with PLATINUM TAQ (Invitrogen Cat#12574018) was used. The RT-PCR reaction contained the following: 25 microliters of 2× reaction mix, 10 microliters of viral RNA template, 1 microliter of 5' primer (10 micromolar), 1 microliter of 3' primer (10 micromolar), 1 microliter of enzyme mix and 12 microliters of nuclease-free distilled water. The primers used in the RT-PCR reactions are listed in Table 3. The reverse transcriptase (RT) reaction was conducted at 50° C. for 30 minutes followed by denaturing at 94° C. for 2 minutes. The PCR reaction was run at 94° C. for 15 seconds, 50° C. for 30 seconds, and 68° C. for 2 minutes for 35 cycles followed by 7 minutes at 68° C. and 4° C. for holding. The RT-PCR DNA product was examined in 1% agarose gel and purified by QIAQUICK gel extraction kit (Qiagen Catalog #28704).

DNA Digestion, Ligation, and Transformation

For DNA digestion, the reaction mix contained 5 microliters of 10× buffer, 4 microliters of BsmB I enzyme (NEB Catalog #R0580L), 12 microliters of water, and either 29 microliters of the purified PCR products from above or 1 microgram of the pAD3000 vector. The digestion reaction was conducted at 55° C. for 60 minutes. RAPID DNA Ligation Kit (Roche Catalog #11635379001) was used for DNA ligation. The ligation mix contained 7 microliters of BsmB I digested HA or NA cDNA, 2 microliters of BsmB I digested vector pAD3000, 10 microliters of 2× buffer, and 1 microliter of ligase. For the negative control, 7 microliters of water was added to 2 microliters of pAD3000, microliters of 2× buffer, and 1 microliter of ligase. After ligation, 5 microliters of ligation mix or control ligation was added to 50 microliters of TOP10 chemically competent *E. coli* cells (Invitrogen Catalog #C4040-03) and put on ice for 30 minutes. The cells were then heat shocked at 42° C. for 30 seconds. The transformed cells were spread on DMEC1 Agar plates containing 100 micrograms/ml Ampicillin (Amp) and incubated overnight at 37° C. Colonies were picked and cultured for expansion in 5 ml of Luria Broth (LB) medium with Amp.

Mini-Prep, DNA Digestion and Sequencing

The plasmid DNA was isolated from the bacterial culture above using the QIAPREP spin miniprep kit (Qiagen Catalog #27106). The DNA samples were eluted in 50 microliters of elution buffer.

The cloned HA and NA plasmids were confirmed by restriction enzyme digestion. Sequence confirmation was performed by Sequetech (Mountain view, Calif.) using sequencing primers 1, 2, and 3 for the HA plasmid and sequencing primer 1 and 2 for the NA plasmid (Table 3).

TABLE 3

Primer Sequences

| Primer | Sequence | Purpose |
| --- | --- | --- |
| HA RT reaction primer | 5' TATTCGTCTCAGGGAGCAAAAGCAGGGGAA (SEQ ID NO: 9) | Reverse transcribe HA RNA into cDNA |
| HA PCR primer 1 | 5' TATTCGTCTCAGGGAGCAAAAGCAGGGGAA (SEQ ID NO: 10) | Amplify HA cDNA |
| HA PCR primer 2 | 5' ATATCGTCTCGTATTAGTAGAAACAAGGGTGTTTTT (SEQ ID NO: 11) | Amplify HA cDNA |
| NA RT reaction primer | 5' TATTCGTCTCAGGGAGCAAAAGCAGGAGT (SEQ ID NO: 12) | Reverse transcribe NA RNA into cDNA |
| NA PCR primer 1 | 5' TATTCGTCTCAGGGAGCAAAAGCAGGAGT (SEQ ID NO: 13) | Amplify NA cDNA |
| NA PCR primer 2 | 5' TATTCGTCTCAGGGAGTAGAAACAAGGAGTTTTT (SEQ ID NO: 14) | Amplify NA cDNA |
| Sequencing primer 1 | 5' TAACTAGAGAACCCACTGCTTACTGGC (SEQ ID NO: 15) | Sequencing cloned HA or NA plasmid |
| Sequencing primer 2 | 5' GGCGCTCCGTGTGTGGCTGCGATGGTG (SEQ ID NO: 16) | Sequencing cloned HA or NA plasmid |
| Sequencing primer 3 | 5' CCCAAGACAAGTTCATGGCC (SEQ ID NO: 17) | Sequencing cloned HA plasmid |
| 125D primers | 5' GACAAGTTCATGGCCCGATCATGACTCGAACAAAG (F) (SEQ ID NO: 18)<br>5' CTTTGTTCGAGTCATGATCGGGCCATGAACTTGTC (R) (SEQ ID NO: 19) | Generate 125D site mutation |
| 127E primers | 5' CATGGCCCAATCATGAATCGAACAAAGGTGTAACG (F) (SEQ ID NO: 20)<br>5' CGTTACACCTTTGTTCGATTCATGATTGGGCCATG (R) (SEQ ID NO: 21) | Generate 127E site mutation |
| 125D/127E primers | 5' GACAAGTTCATGGCCCGATCATGAATCGAACAAAGGTG (F) (SEQ ID NO: 22)<br>5' CACCTTTGTTCGATTCATGATCGGGCCCATGAACTTGTC (R) (SEQ ID NO: 23) | Generate 125D/127E site mutation |

TABLE 3-continued

Primer Sequences

| Primer | Sequence | Purpose |
|---|---|---|
| 125E/127E primers | 5' GACAAGTTCATGGCCCGAACATGAATCGAACAAAGGTG (F) (SEQ ID NO: 24)<br>5' CACCTTTGTTCGATTCATGTTCGGGCCATGAACTTGTC (R) (SEQ ID NO: 25) | Generate 125E/127E site mutation |
| 125E primers | 5' GACAAGTTCATGGCCCGAACATGACTCGAACAAAG (F) (SEQ ID NO: 26)<br>5' CTTTGTTCGAGTCATGTTCGGGCCATGAACTTGTC (R) (SEQ ID NO: 27) | Generate 125E site mutation |

Maxi-Prep

Cells transformed with the HA and NA cDNA clones were cultured in 250 ml of LB broth containing 100 micrograms/ml Amp and plasmid DNA was prepared by the HISPEED plasmid maxi kit (Qiagen Cat#12663).

Mutagenesis

Mutagenesis was performed to introduce mutations into the amino acid sequence of the A/Gilroy/231/2011 virus HA protein. The primers used in the mutagenesis reaction are listed in Table 3. The reaction included 1 microliter of PFU-TURBO polymerase (Stratagene Cat#600250), 1 microliter (0.1 micrograms) of the HA DNA template, 5 microliters of 10× reaction buffer, 2 microliters of the complementary primer pair, 2 microliters of 10 micromolar of dNTP, and 39 microliters of water. The reaction was incubated at 95° C. for 2 minutes followed by 18 cycles of 95° C. for 30 seconds, 50° C. for a minute, and 68° C. for 14 minutes.

Generation of Recombinant Viruses by Reverse Genetics

Rescued (e.g., 6:2 reassortant) viruses were generated by co-transfecting 8 cDNA plasmids encoding the HA and NA of the H1N1 virus and the 6 internal gene segments of cold adapted (ca) A/Ann Arbor/6/60 (MDV-A, master donor virus for type A influenza virus) into co-cultured 293T and MDCK cells. Specifically, 1 microgram of each of the eight plasmids each containing individually DNA encoding one of the following: the HA protein of Gilroy11, the NA protein of Gilroy11, and each of the six internal protein segments of ca A/Ann Arbor/6/60 donor virus, were co-transfected into co-cultured 293T and MDCK cells by TRANSIT-LT1 transfection reagent (Mirus catalog #MIR 2305). Six hours post transfection, the medium was changed and the transfected cells were incubated at 33° C. for 3 days.

Replication of Virus in Eggs

In certain cases, 10 to 11-day-old embryonated chicken eggs were used for viral growth. 100 microliters of culture supernatant from plasmid transfected cells was injected into each egg. The inoculation hole where the egg was injected was sealed with wax, and the eggs were put into a 33° C. incubator. After three days, the eggs were chilled in a 4° C. refrigerator for at least one hour to euthanize the chicken embryo. Then, the egg shell was cracked open at the top and the viruses were harvested by pipette and put into a 50 ml tube. The tubes were spun in a centrifuge at 4000 RPM for 10 minutes to remove the debris. The supernatant was transferred to a new tube. Viruses were stabilized with 10×SPG, aliquoted and stored in a −80° C. freezer. The HA and NA sequences of the reassortant viruses were verified by sequencing of RT-PCR amplified cDNA.

Hemagglutinin (HA Assay)

Viral HA titers were measured in a V-bottomed 96 well plate. To dilute virus, 50 microliters of PBS was added to each well. In the first column, 50 microliters of virus sample was added, mixed and 50 microliters was transferred to the next well on its right. Mixing and transferring of 50 microliters was repeated down the length of the plate. 50 microliters from the last well was discarded into a bleach solution. Next, 50 microliters of 0.5% turkey red blood cells (tRBC) was added to each well, and the plate was placed at room temperature for 30 minutes. If there was a red dot in the center of the well, no hemagglutination occurred and the sample was negative for viruses. If virus agglutinated the RBCs, the RBCs formed a sheet in the well, indicating the presence of virus. By tilting the plate slightly and seeing if the dot starts to make a tear-shaped dot, the titer can be determined. The HA titer is defined as the highest virus dilution that hemagglutinated the RBCs.

Plaque Assay

To determine viral infectious titer, a plaque assay was performed on MDCK cells. Virus dilutions were made by adding 1 ml of PBS into each well of a 96-well block. 111 microliters of virus was added to the first well and mixed. 111 microliters was transferred into the next well, and the pipette tips were changed before each mixing and transferring step. This process was repeated until the last well. 400 microliters of virus dilutions from $10^3$ through $10^6$ dilutions were added to each well of MDCK cells in 6-well plates. The infected monolayer cells were incubated at 37° C. for 1 hour with gentle shaking. Then, the inoculum was removed and 1% agarose with EMEM/L15 medium (SAFC biosciences Catalog #61376) containing 1 microgram/ml of trypsin was added. Once the agarose solidified, the cell plates were put into a 33° C. incubator for 4 days. Because the plaques were small, in certain cases, the plates were further processed by immunostaining. The plates were fixed with 2 ml of 100% methanol and put in a cold room for 30 minutes. Then, the agarose overlay was removed, and 2 ml of methanol was added again to fix the virus plaques for 10 minutes at room temperature. After blocking with 5% milk in PBS, 0.5 ml of primary chicken anti-influenza antibody diluted in milk (1:1000 dilution) was added to the cell plate for 1 hour and the plates were washed three times with PBS. A secondary HRP conjugated anti-chicken antibody (Thermo scientific Cat#31401) diluted 1:1000 was added to the plates. After one hour, the plates were washed three times with PBS. Then, 0.5 ml of AEC substrate chromogen (DAKO Catalog #K3464) was added and the plates were incubated in a 37° C. for 30 minutes. The plates were washed gently with water, and the plaques were counted to determine virus titer.

Example 2

Identification of Residues in the Hemagglutinin Protein of Influenza H1N1 that Enable Viral Growth in Embryonated Chicken Eggs Generation of a Reassortant Virus Wild-type Gilroy11 virus isolated from ferret nasal wash was grown in MDCK cells and eggs. The virus grew better in MDCK cells than in eggs. The HA titer was sometimes detected in amplified MDCK cells but not in eggs. The titer of MDCK amplified wild-type virus was typically about 5-6 $\log_{10}$ PFU/ml.

Figure 2B:
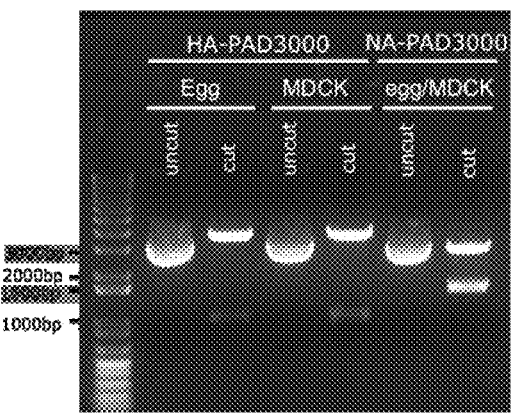

To make a 6:2 reassortant virus from the Gilroy11 viral strain, HA and NA gene segments of Gilroy11 were amplified from the MDCK-amplified and egg-amplified wild-type viruses by RT-PCR and cloned into plasmids, as described in Example 1. The HA and NA plasmids were digested with restriction enzymes and confirmed to have the expected DNA size (FIG. 2B). The HA and NA plasmids were sent to Sequetech for DNA sequencing using HA or NA specific primers and were confirmed to have the identical sequences compared to the vRNA of respective viral stock. A Gilroy11 reassortant virus was generated by reverse genetics technology, i.e., plasmid rescue. After transfecting 8 plasmids encoding the HA and NA of Gilroy11 cloned from MDCK or egg amplified viruses and the six internal protein gene segments from ca A/Ann Arbor/6/60 into 293T/MDCK cells, the transfected cell supernatant was amplified in MDCK cells and embryonated eggs, respectively. After three days of amplification, the presence of the virus in egg allantoic fluid and MDCK cells was examined by an HA assay as described in Example 1. The HA titer was not detected from the egg fluids and the plaque assay showed a very low amount of virus was present in the egg fluids.

Viral Growth Improvement by Amino Acid Changes in the HA Protein

Figure 10A:
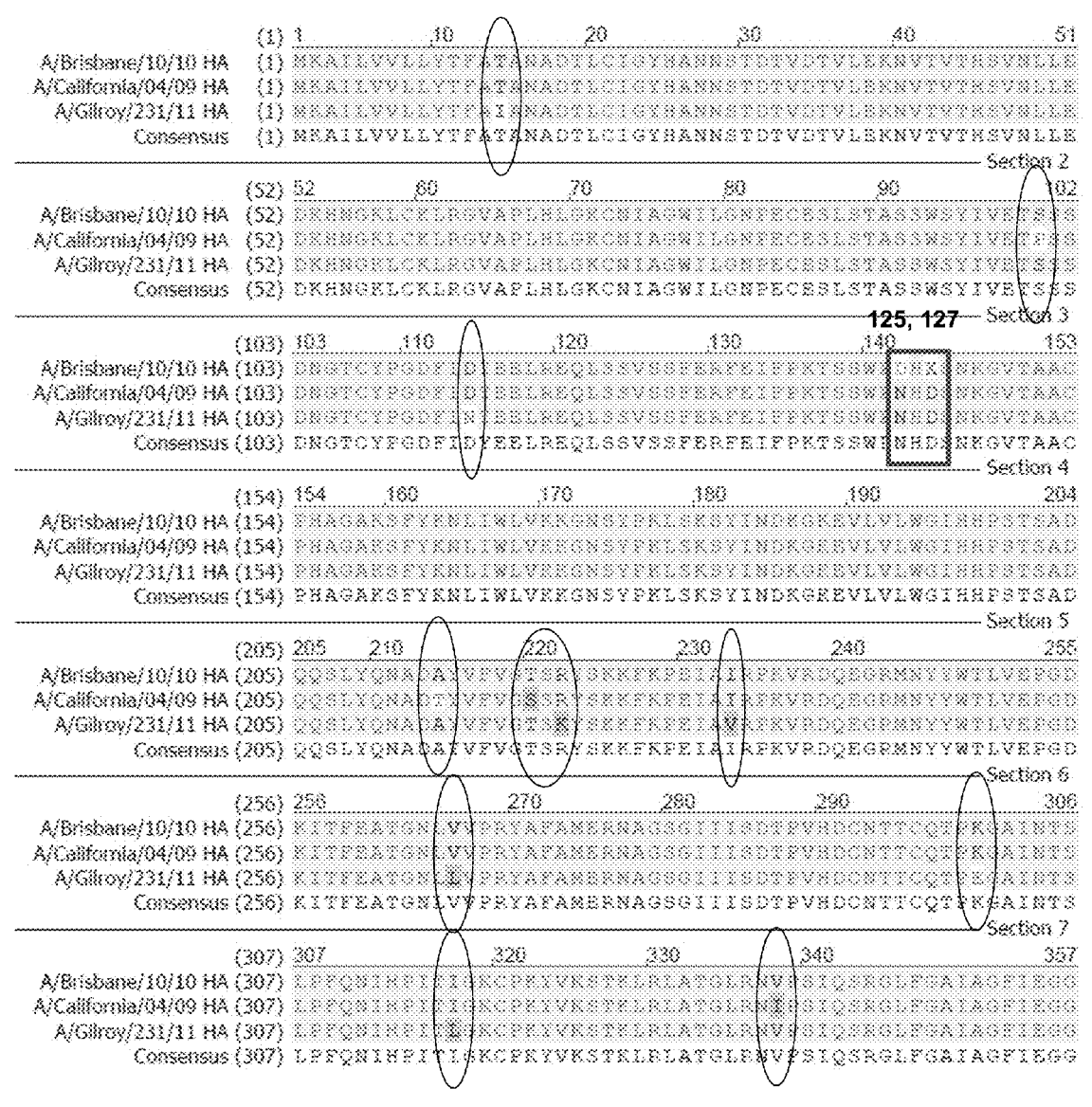

The HA amino acid sequence of Gilroy11 virus was compared with the HA amino acid sequences of A/California/7/09 (CA09) and A/Brisbane/10/10 (Brisbane10) viruses (FIG. 8, FIG. 10). The original (wild-type) CA09 virus did not grow well in eggs. Modified CA09 vaccine strains were generated which contained three amino acid substitutions in the HA amino acid sequence: $K_{119}E$, A186D and D225G (Chen et al., (2010) J. Virol. 84:44-51). Such modified vaccine strains grew better in eggs than the wild-type virus. The three substituted residues are located on the surface of the HA globular head. The substitutions at positions 119 and 186 to acidic residues increased the negative charge on the HA surface. Brisbane10 virus, which was obtained from the CDC, was able to grow in eggs. Comparison of the HA amino acid sequences of the CA09, Brisbane10 and Gilroy11 strains indicated that the amino acid identities at residues 125 and 127 (i.e. D125, E127) were unique for the Brisbane10 virus (Table 4). HA structural analysis revealed that amino acid residues 125 and 127 are on the surface of the HA globular head (FIG. 1A). HA structural analysis also revealed that the N125D/D127E substitutions would change the surface charge of the Gilroy11 HA protein, as shown in FIG. 1B.

To determine whether amino acid substitutions at one or both residues at positions 125 and 127 could improve growth of Gilroy11 virus in eggs, N125D and D127E substitutions were introduced independently or together into the HA amino acid sequence of Gilroy11 virus. To evaluate other acidic residue substitutions, an N125E substitution also was evaluated singly or together with D127E. Specific changes were introduced into the Gilroy11 HA amino acid sequence by site-directed mutagenesis, as described in Example 1. The amino acid substitutions were confirmed by sequencing performed by Sequetech. Recombinant 6:2 reassortant viruses were generated as described in Example 1 and examined. The production of five different modified reassortants was attempted, with each reassortant containing an HA protein with one of the following substitutions or substitution combinations: N125D, N125D/D127E, D127E, N125E/D127E, and N125E. Eggs were infected with transfected cell culture supernatants, as described in Example 1, and incubated for three days. An HA assay was performed on harvested allantoic fluid to determine the presence of virus (i.e. agglutination of turkey RBCs by egg fluids). Of the five HA mutants generated, three reassortant viruses had HA titers that could be detected by the HA assay. Specifically, viruses with substitutions N125D/D127E, D127E, and N125E/D127E in the HA amino acid sequence could be detected after replication in eggs (Table 5). Replication of viruses with the single substitution N125D in the HA amino acid sequence was not detected, in some cases. Viruses with the single substitution N125D or N125E in the HA amino acid sequence were detectably replicated using the HA from egg-amplified wild-type virus but was not detectably replicated if the HA was from cell-amplified wild-type virus.

TABLE 5

Generation of modified H1N1 Gilroy2011 viruses and their replication in eggs

| Gilroy11 | HA 125 | HA 127 | Grow in eggs |
| --- | --- | --- | --- |
| original | N | D | No |
| 1 | D | D | No* |
| 2 | D | E | Yes |
| 3 | N | E | Yes |
| 4 | E | E | Yes |
| 5 | E | D | No* |

*The virus with an HA derived from egg-grown virus replicated in eggs, but an HA from MDCK-grown virus could not replicate in eggs.

Comparison of Virus Replication in Eggs

The data presented in Table 5 indicates that viruses with the D127E substitution grew in eggs. Of the three reassortant viruses that grew, those with a single substitution (i.e. D127E)

TABLE 4

Amino acid differences on the HA protein of H1N1 viruses

| virus | HA amino acid positions and amino acid residues | | | | | | | | | | | | | | |
| --- | --- | --- | --- | --- | --- | --- | --- | --- | --- | --- | --- | --- | --- | --- | --- |
| | 87 | 97 | 119 | 125 | 127 | 186 | 203 | 205 | 216 | 222 | 249 | 283 | 300 | 321 | 374 |
| CA09 | P | D | K | N | D | A | S | R | I | D | V | K | I | I | E |
| CA09 vaccine | | | E | | | D | | | | G | | | | | |
| Brisbane 10 | S | | | D | E | | T | | | | | | | V | K |
| Gilroy11 | S | N | | | | | T | K | V | | L | E | L | V | K |

Figure 3A:
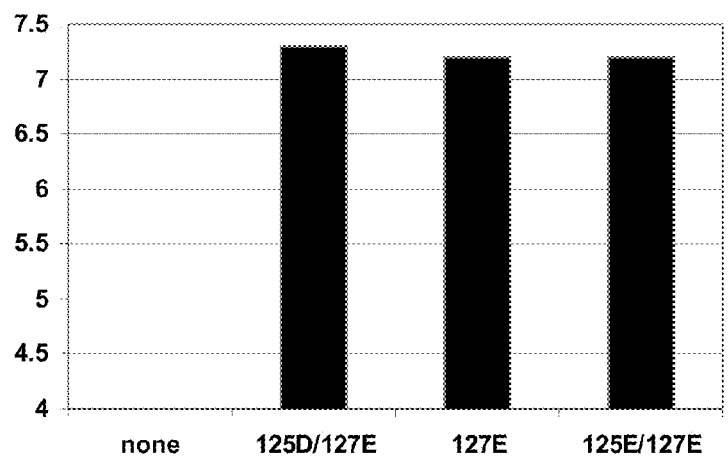
FIG. 3A and FIG. 3B show replication of Gilroy11 viruses with amino acid substitutions at the 125 and 127 positions and their plaque images.
Figure 3B:
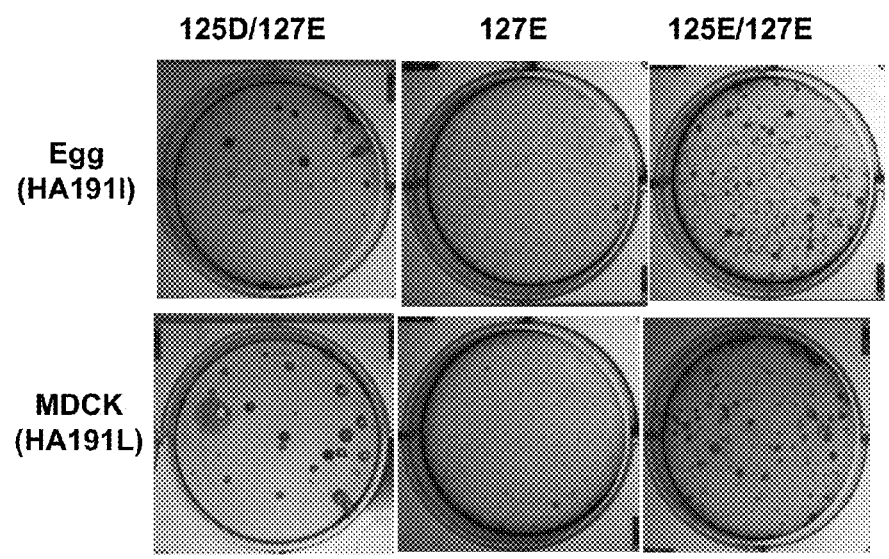

The substituted amino acids in pH1N1 CA09 vaccine strains are in bold and the amino acids that are unique in the Brisbane10 virus are in italics.

in the HA amino acid sequence were compared to those with two substitutions (i.e. N125D/D127E and N125E/D127E) in the HA amino acid sequence using titer analysis and plaque morphology. All three viruses had similar titers (FIG. 3A), however plaques generated from viruses with double mutations (i.e. N125D/D127E and N125E/D127E) were significantly larger than the virus with the single D127E change (FIG. 3B). These results demonstrated that changes to HA amino acid residues 125 and 127 affected viral growth in eggs. The D127E substitution in particular was more effective at improving virus growth in eggs than the substitutions at position 125 for the Gilroy11 virus.

Other reassortant viruses were engineered which included HA and NA polypeptides from different strains in different combinations. The reassortants and their corresponding titer and plaque image data are presented in FIG. 11. The results presented in FIG. 11 indicate that the A/Brisbane/10/10 NA polypeptide increased growth of A/Gilroy/231/2011 virus in eggs and increased virus plaque size in MDCK cells. A comparison of titers for various H1N1 strains, including two from this example (outlined), is presented in FIG. 12. The data indicate that the reassortant containing the A/Gilroy/2011 HA with N125D/D127E substitutions and the NA from A/Brisbane/2011 had a titer close to A/Brisbane/10/10.

Reassortant viruses with additional amino acid changes in the HA of A/Gilroy/231/2011 (e.g., N97D, K205R, V216 μL249V, E283K, and K119E) also were engineered. Growth titers for these reassortants are presented in FIG. 13.

Growth Improvements for Other Viral Strains

Reassortants with A/CA/7/09 HA polypeptides having certain amino acid substitutions described above were also engineered. The replication properties of these reassortants were assessed as above. The results are presented in Table 6 below.

TABLE 6

Titers of the reassortant viruses containing the indicated HA and NA

| | ca virus | Egg virus titer | |
|---|---|---|---|
| HA | NA | log$_{10}$(TCID50/ml) | plaque size |
| A/CA/7/09* | A/CA/7/09 | HA less than 2 | n/a |
| A/CA/7/09* | A/Brisbane/10/10 | HA less than 2 | n/a |
| A/Brisbane/10/10 | A/CA/7/09 | 8.6 | big |
| A/CA/7/09 (N125D) | A/CA/7/09 | 8.2 | big |
| A/CA/7/09 (D127E) | A/CA/7/09 | 7.7 | tiny |
| A/CA/7/09 (N125D + D127E) | A/CA/7/09 | 8.5 | big |
| A/Brisbane/10/10 | A/Brisbane/10/10 | 8.6 | big |

*Original sequence;
n/a: not applicable

The results above indicate that the N125D substitution in the HA polypeptide can significantly improve growth of A/CA/7/09 vaccine virus in eggs. The N125D substitution was more effective at improving virus growth in eggs than the D127E substitution for the A/CA/7/09 virus. Double substitutions at positions 125 and 127 also increased titer in eggs, and improved virus plaque size. The results also show that swapping the A/CA/7/09 HA segment for A/Brisbane/10/10 HA segment affected virus growth in eggs, but swapping the A/CA/7/09 NA segment for A/Brisbane/10/10 NA segment did not affect virus growth in eggs.

Example 3

Examples of Sequences

Provided hereafter are non-limiting examples of certain nucleotide and amino acid sequences.

| Name | Type | SEQ ID NO | Sequence |
|---|---|---|---|
| hemagglutinin (HA) A/Gilroy/231/2011 (mature) | amino acid | 1 | dtlcigyhannstdtvdtvleknvtvthsvnlledkhngklcklrgvaplhlgkcniagwi lgnpeceslstasswsyivetsssdngtcypgdfinyeelreqlssvssferfeifpktss wpnhdsnkgvtaacphagaksfyknliwlvkkgnsypklsksyindkgkevlvlwgihhps tsadqqslyqnadayvfvgtskyskkfkpeiavrpkvrdqefrmnyywtlvepgdkitfea tgnllvpryafamernagsgiiisdtpvhdcnttcqtpegaintslpfqnihpitlgkcpk yvkstkirlatglrnvpsiqsrglfgaiagfieggwtgmvdgwygyhhqneqgsgyaadlk stqnaidkitnkvnsviekmntqftavgkefnhlekrienlnkkvddgfdiwtynaellvl lenertldyhdsnvknlyekvrsqlknnakeigngcfefyhkcdntcmesvkngtydypky seeaklnreeidgvklestriyqilaiystvasslvlvvslgaisfwmcsngslqcrici |
| hemagglutinin (HA) A/Gilroy/231/2011 | nucleic acid | 2 | gtgaaggcaatactagtagttctgctatatacatttgcaaccgcaaatgcagacacattat gtataggttatcatgcgaacaattcaacagacactgtagacacagtactagaaaagaatgt aacagtaacacactctgttaaccttctagaagacaagcataacgggaaattatgcaaacta agaggggtagccccattgcatttgggtaaatgtaacattgctggctggatcctgggaaatc cagagtgtgaatcactctccacagcaagctcatggtcctacattgtggaaacatctagttc agacaatggaacgtgttacccaggagatttcatcgattatgaggagctaagagaacaattg agctcagtgtcatcatttgaaaggtttgagatattcccaagacaagttcatggcccgatc atgamtcgaacaaaggtgtaacggcagcatgtcctcatgctggagcaaaaagcttctacaa aaatttaatatggctagttaaaaaaggaaattcatacccaaagctcagcaaatcctacatt aatgataaagggaaagaagtcctcgtgctatgggcattcaccatccatctactagtgctg accaacaaagtctctatcagaatgcagatgcatatgttttttgtggggacatcaagatacag caagaagttcaagccggaaatagcaataagacccaaagtgagggatcaagaagggagaatg aactattactggacactagtagagccgggagacaaaataacattcgaagcaactggaaatc tagtggtaccgagatatgcattcgcaatggaaagaaatgctggatctggtattatcatttc agatacaccagtccacgattgcaatacaacttgtcagacacccaagggtgctataaacacc agcctcccatttcagaatatacatccgatcacaattggaaaatgtccaaaatatgtaaaaa gcacaaaattgagctggccacaggattgaggaatgtcccgtctattcaatctagaggcct atttggggccattgccggtttcattgaagggggtggacagggatggtagatggatggtac ggttatcaccatcaaaatgagcagggtcaggatatgcagccgacctgaagagcacacaga atgccattgacaagattactaacaaagtaaattctgttattgaaaagatgaatacacagtt cacagcagtaggtaaagagttcaaccacctggaaaaaagaatagagaatttaaataaaaaa gttgatgatggtttcctggacatttggacttacaatgccgaactgttggttctattggaaa atgaaagaactttggactaccacgattcaaatgtgaagaacttatatgaaaaggtaagaag ccagttaaaaaacaatgccaaggaaattggaaacggctgctttgaattttaccacaaatgc gataacacgtgcatggaaagtgtcaaaaatgggacttatgactacccaaaatactcagagg |

| Name | Type | SEQ ID NO | Sequence |
|---|---|---|---|
| | | | aagcaaaattaaacagagaagaaatagatggggtaaagctggaatcaacaaggatttacca gatttggcgatctattcaactgtcgccagttcattggtactggtagtctccctgggggca atcagttctggatgtgctctaatgggtctctacagtgtagaatatgtatttaa |
| neuraminidase (NA) A/Gilroy/231/2011 | amino acid | 3 | mnpnqkiitigsvcmtigmanlilqigniisiwishsiqlgnqsqietcnqsvityenntw vnqtyvnisntnfaagqsvvsvklagnsslcpvsgwaiyskdnsirigskgdvfvirepfi scsplecrtffltqgallndkhsngtikdrspyyrtlmscpigevpspynsrfesvawsasa chdginwltigisgpdngavavlkyngiitdtikswrnsilrtqesecacvngscftimtd gpsdgqasykifriekgkivksvemnapnyhyeescsypdssietcvcrdnwhgsnrpwvs fnqnleyqigyicsgifgdnprpndktgscgpvssngangvkgfsfkygngvwigrtksis srkgremiwdpngwtgtdnnfsikqdivginewsgysgsfvqhpeltgldcirpcfwveli rgrpkentiwtsgssmsfcgvnsdtvgwswpdgaelpftidk |
| neuraminidase (NA) A/Gilroy/231/2011 | nucleic acid | 4 | atgaatccaaaccaaaagataataaccattggttcggtctgtataacaattggaatggcta acttaatattacaaattggaaacataatctcaatatggattagccactcaattcaacttgg gaatcaaaatcagattgaaacatgcaatcaaagcgtcattacttatgaaaacaacacttgg gtaaatcagacatatgttaacatcagcaacaccaacttgctgctggacagtcagtggttt ccgtgaaattagcgggcaattcctctctctgccctgttagtggatgggctatatacagtaa agacaacagatataagaatcggttccaagggggatgtgtttgtcataagggaaccattcat atcatgctcccccttgaatgcgaaaccttcttcttgactcaaggggccttgctaaatgac aaacattccaatggaaccattaaagacaggagcccatatcgaaccctaatgagctgtccta ttggtgaagttccctctccatacaactcaagatttgagtcagtcgcttggtcagcaagtgc ttgtcatgatggcatcagttggctaacaattggaatttctggcccagacaatggggcagtg gctgtgttaaagtacaacggcataataacagacactatcaagagttgggagaaacaatatat tgagaacacaagagtctgaatgtgcatgtgtaaatggttcttgtttttactgtaatgaccga tggaccaagtgatggacaggcctcatacaagatcttcagaatagaaaagggaaagatagtc aaatcagtcgaaatgaataatgcccctaattatcactatgaggaatgctcctgttatcctgatt ctagtgaaatcacatgtgtgtgcagggataactggcatggctcgaatcgaccgtgggtgtc tttcaaccagaatctggaatatcagtataggatacatatgcagtgggattttcggagacaa tccacgcccaatgataagacaggcagttgtggtccagtatcgtctaatggagcaaatgga gtaaaaggatttcattcaaatacggcaatggtgtttggatagggagaactaaaagcatta gttcaagaaacggttttgagatgatttgggatcgaacggatgactgggacagacaataa cttctcaataaagcaagatatcgtaggaataaatgagtggtcaggatatagcgggagtttt gttcagcatccagaactaacagggctggattgtataaaaccttgcttctgggttgaactaa tcagagggcgacccaaagagaacacaatctggactagcgggagcagcatatcctttttgtgg tgtaaacagtgacactgtgggtggtcttggccagacggtgctgagttgccatttaccatt gacaagtaa |
| hemagglutinin (HA) A/Brisbane/10/10 (mature) | amino acid | 5 | dtlcigyhannstdtvdtvleknvtvthsvnlledkhngklcklrgvaplhlgkcniagwi lgnpeceslstasswsyivetsssdngtcypgdfidyeelreqlssvssferfeifpktss wpdhxsnkgvtaacphagaksfyknliwlvkkgnsypklsksyindkgkevlvlwgihhps tsadqqslyqnadayvfvgtsryskkfkpeiairpkvrdqegrmnyywtlvepgdkitfea tgnlvvpryafamernagsgiiisdtpvhdcnttcqtpkgaintslpfqnihpitigkcpk yvkstklrlatglrnvpsiqsrglfgaiagfieggwtgmvdgwygyhhqneqgsgyaadlk stqnaidkitnkvnsviekmntqftavgkefnhlekrienlnkkvddgfldiwtynaellv llenertldyhdsnvknlyekvrsqlknnakeigngcfefyhkcdntcmesvkngtydypk yseeaklnreeidgvklestriyqilaiystvassslvlvvslgaisfwmcsngslqcrici |
| neuraminidase (NA) A/Brisbane/10/10 | amino acid | 6 | mnpnqkiitigsvcitigmanlilqigniisiwishsiqlgnqnqietcnqsvityenntw vnqtyvnisntnfaagqsvvsvklagnsslcpvsgwaiyskdnsirigskgdvfvirepfi scsplecrtffltqgallndkhsngtikdrspyyrtlmscpigevpspynsrfesvawsasa chdgiswltigisgpdngavavlkyngiitdtikswrnnilrtqesecacvngscftvmtd gpsdgqasykifriekgkivksvemnapnyhyeecscypdsseitcvcrdnwhgsnrpwvs fnqnleyqigyicsgifgdnprpndktgscgpvssngangvkgfsfkygngvwigrtksis srngfemiwdpngwtgtdnnfsikqdivginewsgysgsfvqhpeltgldcikpcfwveli rgrpkentiwtsgssisfcgvnsdtvgwswpdgaelpftidk |
| hemagglutinin (HA) A/California/7/09 (mature) | amino acid | 7 | dtl cigyhannst dtvdtvlekn vtvthsvnll edkhngklck lrgvaplhlg kcniagwilg npeceslsta sswsyivetp ssdngtcypg dfidyeelre qlssvssfer feifpktssw pnhdsnkgvt aacphagaks fyknliwlvk kgnsypklsk syindkgkev lvlwgihhps tsadqqslyq nadayvfvgs sryskkfkpe iairpkvrgq egrmnyywtl vepgdkitfe atgnlvvpry afamernags giiisdtpvh dcnttcqtpk gaintslpfq nihpitigkc pkyvkstklr latglrnips iqsrglfgai agfieggwtg mvdgwygyhh qneqgsgyaa dlkstqnaid eitnkvnsvi ekmntqftav qkefnhlekr ienlnkkvdd gfldiwtyna ellvllener tldyhdsnvk nlyekvrsql knnakeigng cfefyhkcdn tcmesvkngt ydypkyseea klnreeidgv klestriyqi laiystvass lvlvvslgai sfwmcsngsl qcrici |
| neuraminidase (NA) A/California/7/09 | amino acid | 8 | mnpnqkiiti gsvcmtigma nlilqignii siwishsiql gnqnietcn qsvityennt wvnqtyvnis ntnfaagqsv vsvklagnss lcpvsgwaiy skdnsvrigs kgdvfvirep fiscsplecr tffltqgall ndkhsngtik drspyrtlms cpigevpspy nsrgesvaws asachdginw ltigisgpdn gavavlkyng iitdtikswr nnilrtqese cacvngscft vmtdgpsngq asykifriek gkivksvemn apnyhyeecs cypdsseitc vcrdnwhgsn rpwvsfnqnl eyqigyicsg ifgdnprpnd ktgscgpvss ngangvkgfs |

-continued

| Name | Type | SEQ ID NO | Sequence |
|---|---|---|---|
| | | | fkygngvwig rtksissrng gemiwdpngw tgtdnnfsik qdivginews gysgsfvqhp eltgldcirp cfwvelirgr pkentiwtsg ssisfcgvns dtvgwswpdg aelpftidk |
| HA RT reaction primer | nucleic acid | 9 | 5' TATTCGTCTCAGGGAGCAAAAGCAGGGGAA |
| HA PCR primer 1 | nucleic acid | 10 | 5' TATTCGTCTCAGGGAGCAAAAGCAGGGGAA |
| HA PCR primer 2 | nucleic acid | 11 | 5' ATATCGTCTCGTATTAGTAGAAACAAGGGTGTTTTT |
| NA RT reaction primer | nucleic acid | 12 | 5' TATTCGTCTCAGGGAGCAAAAGCAGGAGT |
| NA PCR primer 1 | nucleic acid | 13 | 5' TATTCGTCTCAGGGAGCAAAAGCAGGAGT |
| NA PCR primer 2 | nucleic acid | 14 | 5' TATTCGTCTCAGGGAGTAGAAACAAGGAGTTTTT |
| Sequencing primer 1 | nucleic acid | 15 | 5' TAACTAGAGAACCCACTGCTTACTGGC |
| Sequencing primer 2 | nucleic acid | 16 | 5' GGCGCTCCGTGTGTGGCTGCGATGGTG |
| Sequencing primer 3 | nucleic acid | 17 | 5' CCCAAGACAAGTTCATGGCC |
| 125D mutagenesis forward primer | nucleic acid | 18 | 5' GACAAGTTCATGGCCCGATCATGACTCGAACAAAG |
| 125D mutagenesis reverse primer | nucleic acid | 19 | 5' CTTTGTTCGAGTCATGATCGGGCCATGAACTTGTC |
| 127E mutagenesis forward primer | nucleic acid | 20 | 5' CATGGCCCAATCATGAATCGAACAAAGGTGTAACG |
| 127E mutagenesis reverse primer | nucleic acid | 21 | 5' CGTTACACCTTTGTTCGATTCATGATTGGGCCATG |
| 125D/127E mutagenesis forward primer | nucleic acid | 22 | 5' GACAAGTTCATGGCCCGATCATGAATCGAACAAAGGTG |
| 125D/127E mutagenesis reverse primer | nucleic acid | 23 | 5' CACCTTTGTTCGATTCATGATCGGGCCATGAACTTGTC |
| 125E/127E mutagenesis forward primer | nucleic acid | 24 | 5' GACAAGTTCATGGCCCGAACATGAATCGAACAAAGGTG |
| 125E/127E mutagenesis reverse primer | nucleic acid | 25 | 5' CACCTTTGTTCGATTCATGTTCGGGCCATGAACTTGTC |
| 125E mutagenesis forward primer | nucleic acid | 26 | 5' GACAAGTTCATGGCCCGAACATGACTCGAACAAAG |
| 125E mutagenesis forward primer | nucleic acid | 27 | 5' CTTTGTTCGAGTCATGTTCGGGCCATGAACTTGTC |
| hemagglutinin (HA) A/Gilroy/231/2011 (full) | amino acid | 28 | mkailvvllyfaianadtlcigyhannstdtvdtvleknvtvthsvnlledkhngklcklr gvaplhlgkcniagwllgnpeceslstasswsyivetsssdngtcypgdfinyeelreqls svssferfeifpktsswpnhdsnkgvtaacphagaksfyknliwlvkkgnsypklsksyin dkgkevlvlwgihhpstsadqqslyqnadayvfvgtskyskkfkpeiavrpkvrdqegrmn yywtlvepgdkitfeatgnllvpryafamernagsgiiisdtpvhdcnttcqtpegaints lpfqnihpitlgkcpkyvkstklrlatglmvpsiqsrglfgaiagfleggwtgmvdgwygy hhqneqgsgyaadlkstqnaidkitnkvnsviekmntqftavgkefnhlekrienlnkkvd dgfldiwtynaellvllenertldyhdsnvknlyekvrsqlknnakeigngcfefyhkcdn tcmesvkngtdypkyseeaklnreeidgvklestriyqilaiystvasslvlvvslgaisf wmcsngslqvrici |

-continued

| Name | Type | SEQ ID NO | Sequence |
|---|---|---|---|
| hemmagglutinin (HA) A/Brisbane/10/10 (full) | amino acid | 29 | mkailvvllyfatanadtlcigyhannstdtvdtvleknvtvthsvnlledkhngklcklr gvaplhlgkcniagwilgnpeceslstasswsyivetsssdngtcypgdfidyeelreqls svssferfeifpktsswpdhxsnkgvtaacphagaksfyknliwlvkkgnsypklsksyin dkgkevlvlwgihhpstsadqqslyqnadayvfvgtsryskkfkpeiairpkvrdqegrmn yywtlvepgdkitfeatgnlvvpryafamernagsgiiisdtpvhdcnttcqtpkgaints lpfqnihpitigkcpkyvkstklrlatglrnvpsiqsrglfgaiagfieggwtgmvdgwyg yhhqneqgsgyaadlkstqnaidkitnkvnsviekmntqftavgkefnhlekrienlnkkv ddgfldiwtynaellvllenertldyhdsnvknlyekvrsqlknnakeigngcfefhykcd ntcmesvkngtydypkyseeaklnreeidgvklestriyqilaiystvasslvlvvslgai sfwmcsngslqcrici |
| hemagglutinin (HA) A/California/7/09 (full) | amino acid | 30 | mkailvvlly tfatanadtl cigyhannst dtvdtvlekn vtvthsvnll edkhngklck lrgvaplhlg kcniagwilg npeceslsta sswsyivetp ssdngtcypg difdyeelre qlssvssfer feifpktssw pnhdsnkgvt aacphagaks fyknliwlvk kgnsypklsk syindkgkev lvlwgihhps tsadqqslyq nadayvfvgs sryskkfkpe iairpkvrgq egrmnyywtl vepgdkitfe atgnlvvpry afamernags giiisdtpvh dcnttcqtpk gaintslpfq nihpitigkc pkyvkstklr larglrnips iqsrglfgai agfieggwtg mvdgwygyhh qneqgsgyaa dlkstqnaid eitnkvnsvi ekmntqftav gkefnhlekr ienlnkkvdd gfldiwtyna ellvllener tldyhdsnvk nlyekvrsql knnakeigng cfefyhkcdn tcmesvkngt ydypkyseea klnreeidgv klestriyqi laiystvass lvlvvslgai sfwmcsngsl qcrici |

Example 4

Examples of Embodiments

A1. A reassortant influenza virus comprising a first genome segment encoding an isolated or recombinant polypeptide comprising the amino acid sequence of SEQ ID NO:1, or a fragment thereof.

A1.1 The reassortant influenza virus of embodiment A1, wherein the amino acid sequence comprises amino acids 1-327 of SEQ ID NO:1.

A2. The reassortant influenza virus of embodiment A1 or A1.1, wherein the amino acid at position 125 of SEQ ID NO:1 is substituted with a non-native amino acid.

A3. The reassortant influenza virus of any one of embodiments A1 to A2, wherein the amino acid at position 127 of SEQ ID NO:1 is substituted with a non-native amino acid.

A3.1 The reassortant influenza virus of embodiment A2 or A3, wherein the non-native amino acid is an acidic side-chain amino acid.

A4. The reassortant influenza virus of any one of embodiments A1 to A3.1, wherein the amino acid at position 125 of SEQ ID NO:1 is substituted with an aspartic acid (D).

A5. The reassortant influenza virus of any one of embodiments A1 to A3, wherein the amino acid at position 125 of SEQ ID NO:1 is substituted with a glutamic acid (E).

A6. The reassortant influenza virus of any one of embodiments A1 to A3, wherein the amino acid at position 127 of SEQ ID NO:1 is substituted with a glutamic acid (E).

A6.1 The reassortant influenza virus of any one of embodiments A1 to A3, wherein the amino acid at position 125 of SEQ ID NO:1 is substituted with an aspartic acid (D) and the amino acid at position 127 of SEQ ID NO:1 is substituted with a glutamic acid (E).

A6.2 The reassortant influenza virus of any one of embodiments A1 to A3, wherein the amino acid at position 125 of SEQ ID NO:1 is substituted with a glutamic acid (E) and the amino acid at position 127 of SEQ ID NO:1 is substituted with a glutamic acid (E).

A7. The reassortant influenza virus of any one of embodiments A1 to A6.2, wherein the reassortant virus is a 6:2 reassortant virus comprising 6 internal genome segments from one or more donor viruses and a second genome segment encoding a neuraminidase polypeptide.

A7.1 The reassortant influenza virus of embodiment A7, wherein the neuraminidase polypeptide is a swine influenza virus neuraminidase.

A7.2 The reassortant influenza virus of embodiment A7, wherein the neuraminidase polypeptide is an N1 neuraminidase.

A7.3 The reassortant influenza virus of embodiment A7, wherein the neuraminidase polypeptide comprises the amino acid sequence of SEQ ID NO:3, or a fragment thereof.

A7.4 The reassortant influenza virus of embodiment A7, wherein the neuraminidase polypeptide comprises the amino acid sequence of SEQ ID NO:6, or a fragment thereof.

A8. The reassortant influenza virus of any one of embodiments A1 to A6.2, wherein the reassortant virus is a 7:1 reassortant virus comprising 6 internal genome segments and a second genome segment encoding a neuraminidase polypeptide from one or more donor viruses.

A9. The reassortant influenza virus of any one of embodiments A7 to A8, wherein the donor virus comprises one or more phenotypic attributes selected from the group consisting of: attenuated, cold-adapted, and temperature-sensitive.

A10. The reassortant influenza virus of any one of embodiments A7 to A9, wherein the donor virus is selected from the group consisting of: A/Ann Arbor/6/60, A/Puerto Rico/8/34, A/Leningrad/134/17/57, and A/Leningrad/17.

A11. The reassortant influenza virus of any one of embodiments A7 to A10, wherein the virus is a live virus.

A12. An immunogenic composition comprising the reassortant influenza virus of any one of embodiments A1 to A11.

A13. An influenza vaccine comprising the reassortant influenza virus of any one of embodiments A1 to A11.

A14. A live, cold-adapted, temperature-sensitive, attenuated influenza vaccine comprising the reassortant influenza virus of any of embodiments A1 to A11.

B1. A method for increasing the peak titer in embryonated eggs for a reassortant or recombinant influenza virus comprising a hemagglutinin polypeptide, comprising substituting one or more amino acid residues of the hemagglutinin polypeptide at position 125 and/or 127 of SEQ ID NO:1 with non-native amino acid residues, thereby increasing the peak titer in embryonated eggs for the influenza virus.

B1.1 The method of embodiment B1, wherein the non-native amino acid is an acidic side-chain amino acid.

B2. The method of embodiment B1 or B1.1, wherein the amino acid residue at position 125 of SEQ ID NO:1 is substituted with an aspartic acid (D).

B3. The method of embodiment B1, wherein the amino acid residue at position 125 of SEQ ID NO:1 is substituted with a glutamic acid (E).

B4. The method of embodiment B1, wherein the amino acid residue at position 127 of SEQ ID NO:1 is substituted with a glutamic acid (E).

B4.1 The method of embodiment B1, wherein the amino acid at position 125 of SEQ ID NO:1 is substituted with an aspartic acid (D) and the amino acid at position 127 of SEQ ID NO:1 is substituted with a glutamic acid (E).

B4.2 The method of embodiment B1, wherein the amino acid at position 125 of SEQ ID NO:1 is substituted with a glutamic acid (E) and the amino acid at position 127 of SEQ ID NO:1 is substituted with a glutamic acid (E).

B5. The method of any one of embodiments B1 to B4.2, wherein the reassortant or recombinant influenza virus is a 6:2 reassortant virus comprising 6 internal genome segments of a donor virus selected from the group consisting of A/Ann Arbor/6/60, A/Puerto Rico/8/34, A/Leningrad/134/17/57, and A/Leningrad/17.

B5.1 The method of any one of embodiments B1 to B5, wherein the reassortant or recombinant influenza virus comprises a neuraminidase polypeptide comprising the amino acid sequence of SEQ ID NO:6.

B6. The method of any one of embodiments B1 to B4, wherein the reassortant or recombinant influenza virus is a 7:1 reassortant virus comprising 7 genome segments of a donor virus selected from the group consisting of A/Ann Arbor/6/60, A/Puerto Rico/8/34, A/Leningrad/134/17/57, and A/Leningrad/17.

B7. The method of any one of embodiments B1 to B6, wherein the reassortant or recombinant influenza virus comprises one or more phenotypic attributes selected from the group consisting of: attenuated, cold-adapted and temperature-sensitive.

B8. The method of any one of embodiments B1 to B7, wherein the peak titer in embryonated eggs for the reassortant or recombinant influenza virus is increased at least 1.5-fold relative to the same reassortant or recombinant influenza virus not comprising the one or more amino acid substitutions.

B9. The method of any one of embodiments B1 to B7, wherein the peak titer in embryonated eggs for the reassortant or recombinant influenza virus is increased at least 2-fold relative to the same reassortant or recombinant influenza virus not comprising the one or more amino acid substitutions.

B10. The method of any one of embodiments B1 to B7, wherein the peak titer in embryonated eggs for the reassortant or recombinant influenza virus is increased at least 4-fold relative to the same reassortant or recombinant influenza virus not comprising the one or more amino acid substitutions.

B11. The method of any one of embodiments B1 to B7, wherein the peak titer in embryonated eggs for the reassortant or recombinant influenza virus is increased at least 10-fold relative to the same reassortant or recombinant influenza virus not comprising the one or more amino acid substitutions.

B12. An immunogenic composition comprising the reassortant or recombinant influenza virus of any one of embodiments B1 to B11.

B13. An influenza vaccine comprising the reassortant or recombinant influenza virus of any one of embodiments B1 to B11.

B14. A live, cold-adapted, temperature-sensitive, attenuated influenza vaccine comprising the reassortant or recombinant influenza virus of any of embodiments B1 to B11.

C1. An isolated or recombinant polypeptide comprising the amino acid sequence of SEQ ID NO:1 or fragment thereof.

C1.1 The polypeptide of embodiment C1, wherein the amino acid sequence comprises amino acids 1-327 of SEQ ID NO:1.

C2. The polypeptide of embodiment C1 or C1.1, wherein the amino acid at position 125 of SEQ ID NO:1 is substituted with a non-native amino acid.

C3. The polypeptide of any one of embodiments C1 to C2, wherein the amino acid at position 127 of SEQ ID NO:1 is substituted with a non-native amino acid.

C3.1 The polypeptide of embodiments C2 or C3, wherein the non-native amino acid is an acidic side-chain amino acid.

C4. The polypeptide of any one of embodiments C1 to C3.1, wherein the amino acid at position 125 of SEQ ID NO:1 is substituted with an aspartic acid (D).

C5. The polypeptide of any one of embodiments C1 to C3, wherein the amino acid at position 125 of SEQ ID NO:1 is substituted with a glutamic acid (E).

C6. The polypeptide of any one of embodiments C1 to C3, wherein the amino acid at position 127 of SEQ ID NO:1 is substituted with a glutamic acid (E).

C6.1 The polypeptide of any one of embodiments C1 to C3, wherein the amino acid at position 125 of SEQ ID NO:1 is substituted with an aspartic acid (D) and the amino acid at position 127 of SEQ ID NO:1 is substituted with a glutamic acid (E).

C6.2 The polypeptide of any one of embodiments C1 to C3, wherein the amino acid at position 125 of SEQ ID NO:1 is substituted with a glutamic acid (E) and the amino acid at position 127 of SEQ ID NO:1 is substituted with a glutamic acid (E).

C7. An immunogenic composition comprising the polypeptide of any one of embodiments C1 to C6.2.

C8. An isolated or recombinant nucleic acid comprising a nucleotide sequence encoding the polypeptide of any one of embodiments C1 to C6.2.

C9. An immunogenic composition comprising the nucleic acid of embodiment C8.

D1. A reassortant influenza virus comprising a first genome segment encoding a modified hemagglutinin polypeptide wherein,
  (a) the amino acid at position 125, or a position corresponding to residue 125 of SEQ ID NO:1, is substituted with a non-native amino acid, and/or
  (b) the amino acid at position 127, or a position corresponding to residue 127 of SEQ ID NO:1, is substituted with a non-native amino acid.

D1.1 The reassortant influenza virus of embodiment D1, wherein the non-native amino acid is an acidic side-chain amino acid.

D2. The reassortant influenza virus of embodiment D1 or D1.1, wherein the unmodified hemagglutinin polypeptide comprises the amino acid sequence of SEQ ID NO:1, or a fragment thereof.

D2.1 The reassortant influenza virus of embodiment D2, wherein the amino acid sequence comprises amino acids 1-327 of SEQ ID NO:1.

D3. The reassortant influenza virus of embodiment D1, wherein the unmodified hemagglutinin polypeptide comprises the amino acid sequence of SEQ ID NO:7, or a fragment thereof.

D3.1 The reassortant influenza virus of embodiment D3, wherein the amino acid sequence comprises amino acids 1-327 of SEQ ID NO:7.

D4. The reassortant influenza virus of any one of embodiments D1 to D3.1, wherein the amino acid at position 125 is substituted with an aspartic acid (D).

D5. The reassortant influenza virus of any one of embodiments D1 to D3.1, wherein the amino acid at position 125 is substituted with a glutamic acid (E).

D6. The reassortant influenza virus of any one of embodiments D1 to D3.1, wherein the amino acid at position 127 is substituted with a glutamic acid (E).

D6.1 The reassortant influenza virus of any one of embodiments D1 to D3.1, wherein the amino acid at position 125 is substituted with an aspartic acid (D) and the amino acid at position 127 is substituted with a glutamic acid (E).

D6.2 The reassortant influenza virus of any one of embodiments D1 to D3.1, wherein the amino acid at position 125 is substituted with a glutamic acid (E) and the amino acid at position 127 is substituted with a glutamic acid (E).

D7. The reassortant influenza virus of any one of embodiments D1 to D6.2, wherein the reassortant virus is a 6:2 reassortant virus comprising 6 internal genome segments from one or more donor viruses and a second genome segment encoding a neuraminidase polypeptide.

D7.1 The reassortant influenza virus of embodiment D7, wherein the neuraminidase polypeptide is a swine influenza virus neuraminidase.

D7.2. The reassortant influenza virus of embodiment D7, wherein the neuraminidase polypeptide is an N1 neuraminidase.

D7.3 The reassortant influenza virus of embodiment D7, wherein the neuraminidase polypeptide comprises the amino acid sequence of SEQ ID NO:3 or SEQ ID NO:8, or a fragment thereof.

D7.4 The reassortant influenza virus of embodiment D7, wherein the neuraminidase polypeptide comprises the amino acid sequence of SEQ ID NO:6, or a fragment thereof.

D8. The reassortant influenza virus of any one of embodiments D1 to D6.2, wherein the reassortant virus is a 7:1 reassortant virus comprising 6 internal genome segments and a second genome segment encoding a neuraminidase polypeptide from one or more donor viruses.

D9. The reassortant influenza virus of any one of embodiments D7 to D8, wherein the donor virus comprises one or more phenotypic attributes selected from the group consisting of: attenuated, cold-adapted, and temperature-sensitive.

D10. The reassortant influenza virus of any one of embodiments D7 to D9, wherein the donor virus is selected from the group consisting of: A/Ann Arbor/6/60, A/Puerto Rico/8/34, A/Leningrad/134/17/57, and A/Leningrad/17.

D11. The reassortant influenza virus of any one of embodiments D7 to D10, wherein the virus is a live virus.

D12. An immunogenic composition comprising the reassortant influenza virus of any one of embodiments D1 to D11.

D13. An influenza vaccine comprising the reassortant influenza virus of any one of embodiments D1 to D11.

D14. A live, cold-adapted, temperature-sensitive, attenuated influenza vaccine comprising the reassortant influenza virus of any of embodiments D1 to D11.

E1. A method for increasing the peak titer in embryonated eggs for a reassortant or recombinant influenza virus comprising a hemagglutinin polypeptide, comprising substituting one or more amino acid residues of the hemagglutinin polypeptide at position 125, or a residue corresponding to position 125 of SEQ ID NO:1, and/or at position 127, or a residue corresponding to position 127 of SEQ ID NO:1, with non-native amino acid residues, thereby increasing the peak titer in embryonated eggs for the influenza virus.

E1.1 The method of embodiment E1, wherein the non-native amino acid is an acidic side-chain amino acid.

E2. The method of embodiment E1 or E1.1, wherein the amino acid residue at position 125 is substituted with an aspartic acid (D).

E3. The method of embodiment E1, wherein the amino acid residue at position 125 is substituted with a glutamic acid (E).

E4. The method of embodiment E1, wherein the amino acid residue at position 127 is substituted with a glutamic acid (E).

E4.1 The method of embodiment E1, wherein the amino acid at position 125 is substituted with an aspartic acid (D) and the amino acid at position 127 is substituted with a glutamic acid (E).

E4.2 The method of embodiment E1, wherein the amino acid at position 125 is substituted with a glutamic acid (E) and the amino acid at position 127 is substituted with a glutamic acid (E).

E5. The method of any one of embodiments E1 to E4.2, wherein the reassortant or recombinant influenza virus is a 6:2 reassortant virus comprising 6 internal genome segments of a donor virus selected from the group consisting of A/Ann Arbor/6/60, A/Puerto Rico/8/34, A/Leningrad/134/17/57, and A/Leningrad/17.

E5.1 The method of any one of embodiments E1 to E5, wherein the reassortant or recombinant influenza virus comprises a neuraminidase polypeptide comprising the amino acid sequence of SEQ ID NO:6.

E6. The method of any one of embodiments E1 to E4.2, wherein the reassortant or recombinant influenza virus is a 7:1 reassortant virus comprising 7 genome segments of a donor virus selected from the group consisting of A/Ann Arbor/6/60, A/Puerto Rico/8/34, A/Leningrad/134/17/57, and A/Leningrad/17.

E7. The method of any one of embodiments E1 to E6, wherein the reassortant or recombinant influenza virus comprises one or more phenotypic attributes selected from the group consisting of: attenuated, cold-adapted and temperature-sensitive.

E8. The method of any one of embodiments E1 to E7, wherein the peak titer in embryonated eggs for the reassortant or recombinant influenza virus is increased at least 1.5-fold relative to the same reassortant or recombinant influenza virus not comprising the one or more amino acid substitutions.

E9. The method of any one of embodiments E1 to E7, wherein the peak titer in embryonated eggs for the reassortant or recombinant influenza virus is increased at least 2-fold relative to the same reassortant or recombinant influenza virus not comprising the one or more amino acid substitutions.

E10. The method of any one of embodiments E1 to E7, wherein the peak titer in embryonated eggs for the reassortant or recombinant influenza virus is increased at least 4-fold relative to the same reassortant or recombinant influenza virus not comprising the one or more amino acid substitutions.

E11. The method of any one of embodiments E1 to E7, wherein the peak titer in embryonated eggs for the reassortant or recombinant influenza virus is increased at least 10-fold relative to the same reassortant or recombinant influenza virus not comprising the one or more amino acid substitutions.

E12. An immunogenic composition comprising the reassortant or recombinant influenza virus of any one of embodiments E1 to E11.

E13. An influenza vaccine comprising the reassortant or recombinant influenza virus of any one of embodiments E1 to E11.

E14. A live, cold-adapted, temperature-sensitive, attenuated influenza vaccine comprising the reassortant or recombinant influenza virus of any of embodiments E1 to E11.

F1. An isolated or recombinant modified hemagglutinin polypeptide, or a fragment thereof, wherein,
- (a) the amino acid at position 125, or a position corresponding to residue 125 of SEQ ID NO:1, is substituted with a non-native amino acid, and/or
- (b) the amino acid at position 127, or a position corresponding to residue 127 of SEQ ID NO:1, is substituted with a non-native amino acid.

F1.1 The polypeptide of embodiment F1, wherein the non-native amino acid is an acidic side-chain amino acid.

F2. The polypeptide of embodiment F1 or F1.1, wherein the unmodified hemagglutinin polypeptide comprises the amino acid sequence of SEQ ID NO:1, or a fragment thereof.

F2.1 The polypeptide of embodiment F2, wherein the amino acid sequence comprises amino acids 1-327 of SEQ ID NO:1.

F3. The polypeptide of embodiment F1, wherein the unmodified hemagglutinin polypeptide comprises the amino acid sequence of SEQ ID NO:7, or a fragment thereof.

F3.1 The polypeptide of embodiment F3, wherein the amino acid sequence comprises amino acids 1-327 of SEQ ID NO:7.

F4. The polypeptide of any one of embodiments F1 to F3.1, wherein the amino acid at position 125 is substituted with an aspartic acid (D).

F5. The polypeptide of any one of embodiments F1 to F3.1, wherein the amino acid at position 125 is substituted with a glutamic acid (E).

F6. The polypeptide of any one of embodiments F1 to F3.1, wherein the amino acid at position 127 is substituted with a glutamic acid (E).

F6.1 The polypeptide of any one of embodiments F1 to F3.1, wherein the amino acid at position 125 is substituted with an aspartic acid (D) and the amino acid at position 127 is substituted with a glutamic acid (E).

F6.2 The polypeptide of any one of embodiments F1 to F3.1, wherein the amino acid at position is substituted with a glutamic acid (E) and the amino acid at position 127 is substituted with a glutamic acid (E).

F7. An immunogenic composition comprising the polypeptide of any one of embodiments F1 to F6.2.

F8. An isolated or recombinant nucleic acid comprising a nucleotide sequence encoding the polypeptide of any one of embodiments F1 to F6.2.

F9. An immunogenic composition comprising the nucleic acid of embodiment F8.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A reassortant influenza virus comprising at least 6 internal genome segments from one or more master donor viruses and a first genome segment encoding a hemagglutinin polypeptide comprising an amino acid sequence selected from the group consisting of:
   (a) SEQ ID NO:1;
   (b) a modified SEQ ID NO:1, wherein the amino acid at position 125 is substituted with an aspartic acid (D) or a glutamic acid (E);
   (c) a modified SEQ ID NO:1, wherein the amino acid at position 127 is substituted with a glutamic acid (E); and
   (d) a modified SEQ ID NO:1, wherein the amino acid at position 125 is substituted with an aspartic acid (D) or a glutamic acid (E) and the amino acid at position 127 is substituted with a glutamic acid (E); wherein the six internal genome segments and the hemagglutinin encoding genome segment are from different influenza viruses.

2. The reassortant influenza virus of claim 1, wherein the amino acid sequence comprises amino acids 1-327 of SEQ ID NO:1 or amino acids 1-327 of a modified SEQ ID NO:1 according to (b), (c) or (d).

3. The reassortant influenza virus of claim 1, wherein the first genome segment produces a polynucleotide encoding the hemagglutinin polypeptide, wherein the polynucleotide comprises a nucleotide sequence of:
   (i) SEQ ID NO:2, which encodes a hemagglutinin polypeptide according to (a), or (ii) a modified SEQ ID NO:2, which encodes a hemagglutinin polypeptide according to (b), (c) or (d).

4. The reassortant influenza virus of claim 1, wherein the reassortant virus is a 6:2 reassortant virus comprising 6 internal genome segments from one or more master donor viruses and a second genome segment encoding a neuraminidase polypeptide.

5. The reassortant influenza virus of claim 4, wherein the neuraminidase polypeptide comprises the amino acid sequence of SEQ ID NO:3, or the amino acid sequence of SEQ ID NO:6.

6. The reassortant influenza virus of claim 4, wherein the master donor virus comprises one or more phenotypic attributes selected from the group consisting of: attenuated, cold-adapted, and temperature-sensitive.

7. The reassortant influenza virus of claim 6, wherein the master donor virus is selected from the group consisting of: A/Ann Arbor/6/60, A/Puerto Rico/8/34, A/Leningrad/134/17/57, and A/Leningrad/17.

8. The reassortant influenza virus of claim 1, wherein the reassortant virus is a 7:1 reassortant virus comprising 6 internal genome segments and a second genome segment encoding a neuraminidase polypeptide from one or more master donor viruses.

9. The reassortant influenza virus of claim 8, wherein the master donor virus comprises one or more phenotypic attributes selected from the group consisting of: attenuated, cold-adapted, and temperature-sensitive.

10. The reassortant influenza virus of claim 9, wherein the master donor virus is selected from the group consisting of: A/Ann Arbor/6/60, A/Puerto Rico/8/34, A/Leningrad/134/17/57, and A/Leningrad/17.

11. The reassortant influenza virus of claim 1, wherein the virus is a live virus.

12. An immunogenic composition comprising the reassortant influenza virus of claim 1.

13. An influenza vaccine comprising the reassortant influenza virus of claim 1.

14. A live, cold-adapted, temperature-sensitive, attenuated influenza vaccine comprising the reassortant influenza virus of claim 1.

15. A method for increasing the peak titer in embryonated eggs for a reassortant or recombinant influenza virus comprising a hemagglutinin polypeptide, comprising:
   (a) substituting an amino acid residue of the hemagglutinin polypeptide at position 125, or a residue corresponding to position 125 of SEQ ID NO:1, with an aspartic acid (D) or a glutamic acid (E);
   (b) substituting an amino acid residue of the hemagglutinin polypeptide at position 127, or a residue corresponding to position 127 of SEQ ID NO:1, with a glutamic acid (E); or
   (c) substituting an amino acid residue of the hemagglutinin polypeptide at position 125, or a residue corresponding to position 125 of SEQ ID NO:1, with an aspartic acid (D) or a glutamic acid (E) and substituting an amino acid residue of the hemagglutinin polypeptide at position 127, or a residue corresponding to position 127 of SEQ ID NO:1, with a glutamic acid (E),
   thereby increasing the peak titer in embryonated eggs for the influenza virus.

16. An isolated or recombinant hemagglutinin polypeptide comprising:
   (a) a modified amino acid sequence, wherein the amino acid at position 125, or a position corresponding to residue 125 of SEQ ID NO:1, is substituted with an aspartic acid (D) or a glutamic acid (E);
   (b) a modified amino acid sequence, wherein the amino acid at position 127, or a position corresponding to residue 127 of SEQ ID NO:1, is substituted with a glutamic acid (E); or
   (c) a modified amino acid sequence, wherein the amino acid at position 125, or a position corresponding to residue 125 of SEQ ID NO:1, is substituted with an aspartic acid (D) or a glutamic acid (E), and wherein the amino acid at position 127, or a position corresponding to residue 127 of SEQ ID NO:1, is substituted with a glutamic acid (E).

17. An isolated polynucleotide encoding the hemagglutinin polypeptide of claim 16.

18. A reassortant influenza virus comprising a first genome segment encoding a modified hemagglutinin polypeptide wherein:
   (a) the amino acid at position 125, or a position corresponding to residue 125 of SEQ ID NO:1, is substituted with an aspartic acid (D) or a glutamic acid (E);
   (b) the amino acid at position 127, or a position corresponding to residue 127 of SEQ ID NO:1, is substituted with a glutamic acid (E); or
   (c) the amino acid at position 125, or a position corresponding to residue 125 of SEQ ID NO:1, is substituted with an aspartic acid (D) or a glutamic acid (E) and the amino acid at position 127, or a position corresponding to residue 127 of SEQ ID NO:1, is substituted with a glutamic acid (E).

19. A method for producing a reassortant influenza virus in cell culture, the method comprising:
   (a) introducing a plurality of vectors into a population of host cells capable of supporting replication of influenza viruses, which plurality of vectors comprises nucleotide sequences corresponding to at least 6 internal genome segments of a master donor virus; and one genome segment encoding a hemagglutinin polypeptide comprising the amino acid sequence of:
      (i) SEQ ID NO:1;
      (ii) a modified SEQ ID NO:1, wherein the amino acid at position 125 is substituted with an aspartic acid (D) or a glutamic acid (E), or a fragment thereof;
      (iii) a modified SEQ ID NO:1, wherein the amino acid at position 127 is substituted with a glutamic acid (E); or
      (iv) a modified SEQ ID NO:1, wherein the amino acid at position 125 is substituted with an aspartic acid (D) or a glutamic acid (E) and the amino acid at position 127 is substituted with a glutamic acid (E); wherein the 6 internal genome segments and the hemagglutinin encoding genome segment are from different influenza viruses;
   (b) culturing the population of host cells; and
   (c) recovering the influenza virus.

* * * * *